(12) United States Patent
Xiao et al.

(10) Patent No.: US 11,043,745 B2
(45) Date of Patent: Jun. 22, 2021

(54) RESISTIVELY LOADED DIELECTRIC BICONICAL ANTENNAS FOR NON-INVASIVE TREATMENT

(71) Applicant: Old Dominion University Research Foundation, Norfolk, VA (US)

(72) Inventors: Shu Xiao, Norfolk, VA (US); Xianbing Zou, Chengdu (CN)

(73) Assignee: OLD DOMINION UNIVERSITY RESEARCH FOUNDATION, Norfolk, VA (US)

( * ) Notice: Subject to any disclaimer, the term of this patent is extended or adjusted under 35 U.S.C. 154(b) by 101 days.

(21) Appl. No.: 16/273,112

(22) Filed: Feb. 11, 2019

(65) Prior Publication Data
US 2020/0259261 A1    Aug. 13, 2020

(51) Int. Cl.
| | | |
|---|---|---|
| *A61N 1/08* | (2006.01) | |
| *A61N 1/28* | (2006.01) | |
| *H01P 3/16* | (2006.01) | |
| *H01Q 9/04* | (2006.01) | |
| *H01Q 13/24* | (2006.01) | |
| *A61N 1/36* | (2006.01) | |
| *A61N 1/372* | (2006.01) | |

(52) U.S. Cl.
CPC ............ *H01Q 9/0485* (2013.01); *H01P 3/16* (2013.01); *A61N 1/08* (2013.01); *A61N 1/36178* (2013.01); *A61N 1/37235* (2013.01); *H01Q 13/24* (2013.01)

(58) Field of Classification Search
CPC ...... H01Q 9/0485; H01Q 13/24; H01Q 19/08; H01Q 13/0266; H01P 3/16; H01P 5/087; A61N 1/36178; A61N 1/37235; A61N 1/08; A61N 1/403; A61N 1/36175; A61N 1/36153; A61N 1/40; A61N 1/06; A61N 1/28

See application file for complete search history.

(56) References Cited

U.S. PATENT DOCUMENTS

| | | | |
|---|---|---|---|
| 6,326,177 B1 | 12/2001 | Schoenbach et al. | |
| 6,432,050 B1 | 8/2002 | Porat et al. | |
| 6,829,509 B1 * | 12/2004 | MacDonald | A61N 1/3718 607/119 |
| 7,118,590 B1 * | 10/2006 | Cronin | A61B 18/18 607/105 |

(Continued)

OTHER PUBLICATIONS

Altunc et al; Design of a special dielectric lens for concentrating a subnanosecond electronmagnetic pulse on a biological target; IEEE Transactions on Dielectrics and Electrical Insulation; 16 (5); pp. 1364-1375; Oct. 2009.

(Continued)

*Primary Examiner* — Minh D A
(74) *Attorney, Agent, or Firm* — Shay Glenn LLP

(57) ABSTRACT

Resistively loaded dielectric biconical antenna apparatuses, including systems and devices, that may be used to transmit very short electrical pulses (e.g., nanosecond, sub-nanosecond, picosecond, etc.) into tissue non-invasively at energy levels sufficient to invoke biological changes in the tissue. These resistively loaded dielectric biconical antenna apparatuses may include a resistor ring reducing internal reflection and reducing energy loss, as well as delivering longer pulses (e.g. microsecond to millisecond) to tissue.

24 Claims, 21 Drawing Sheets

(56) References Cited

U.S. PATENT DOCUMENTS

| | | | |
|---|---|---|---|
| 8,000,813 B2* | 8/2011 | Schoenbach | A61N 1/40 607/154 |
| 8,512,334 B2 | 8/2013 | Nuccitelli et al. | |
| 8,822,222 B2 | 9/2014 | Beebe et al. | |
| 9,101,764 B2 | 8/2015 | Nuccitelli et al. | |
| 9,168,373 B2 | 10/2015 | Nuccitelli et al. | |
| 9,333,368 B2 | 5/2016 | Xiao et al. | |
| 9,724,155 B2 | 8/2017 | Nuccitelli et al. | |
| 2003/0011533 A1 | 1/2003 | Sakurada et al. | |
| 2008/0103529 A1* | 5/2008 | Schoenbach | C12M 35/02 607/2 |
| 2012/0283534 A1 | 11/2012 | Carr et al. | |
| 2013/0194540 A1 | 8/2013 | Pugh et al. | |
| 2014/0364797 A1* | 12/2014 | Schoenbach | A61N 5/025 604/20 |
| 2015/0201991 A1 | 7/2015 | Zemlin | |
| 2017/0245928 A1 | 8/2017 | Xiao et al. | |
| 2018/0078755 A1 | 3/2018 | Kreis et al. | |
| 2019/0046791 A1 | 2/2019 | Ebbers et al. | |
| 2019/0217080 A1 | 7/2019 | Moss et al. | |

OTHER PUBLICATIONS

Altunc et al.; Focal waveforms for various source waveforms driving a prolate-spheroidal impulse radiating antenna (IRA); Radio Science; 43(4); RS4S13; 9 pages, doi:10.1029/200RS003775; Aug. 1, 2008.

Attal, et al., EFNS guidelines on pharmacological treatment of neuropathic pain, European Journal of Neurology; vol. 13 13(11); pp. 1153-1169, Nov. 2006.

Bajracharya et al.; Target detection with impulse radiating antenna; IEEE Antennas and Wireless Propagation Letters; vol. 10; pp. 496-499; May 19, 2011.

Baum et al; JOLT: A highly directive, very intensive, impulse-like radiator; Proceedings of the IEEE; 92 (7); pp. 1096-1109; Jul. 2004.

Baum; Focal waveform of a prolate-spheroidal impulse-radiating antenna (IRA); Radio Science; 42 (6), 11 pages; Doi: 10.1029/2006RS003556; Dec. 2007.

Brown et al.; Motor cortex stimulation; Pain Medicine; 7 (S1); pp. S140-S145; downloaded from (https://academic.oup.com/painmedicine/article-abstract/7/suppl_1/S140/1817160); Dec. 21, 2017.

Burfeindt et al.; Microwave beamforming for non-invasive patient-specific hyperthermia treatment of pediatric brain cancer; Physics in Medicine and Biology; 56 (9); pp. 2743-2754; Apr. 5, 2011.

Clement et al.; A noninvasive method for focusing ultrasound through the human skull; Physics in Medicine and Biology; 47(8); pp. 1219-1236; Apr. 5, 2002.

Cruccu et al.; EFNS guidelines on neurostimulation therapy for neuropathic pain; European Journal of Neurology; 14(9); 19 pages; Doi: 10/1111/j. 1468-1331.2007.0196.x; Sep. 2007.

Dunn et al.; FDTD verification of deep-set brain tumor hyperthermia using a spherical microwave source distribution; IEEE Transactions on Microwave Theory and Techniques; 44(10); pp. 1769-1777; Oct. 1996.

Gabriel; 2007. Dielectric Properties of Biological Material; Handbook of Biological Effects of Electromagnetic Fields; Bioengineering and Biophysical Aspects of Electromagnetic Fields; 3rd. Edition, Edited by F.S. Barnes and B. Greenbaum; CRC press; pp. 52-94; (year of pub. sufficiently earlier than effective US filing date and any foreign priority date) 2007.

Gavrilov; Use of focused ultrasound for stimulation of nerve structures; Ultrasonics 22(3), pp. 132-138; May 1, 1984.

Gouzouasis et al.; Contactless passive diagnosis for brain intracranial applications: a study using dielectric matching materials; Bioelectromagnetics; 31(5); pp. 335-349; 11 pages; Doi: 10.1002/bem.20572; Jul. 2010.

Ibey et al.; Plasma membrane permeabilization by 60- and 600-ns electric pulses is determined by the absorbed dose; Bioelectromagnetics: Journal of the Bioelectromagnetics Society, The Society for Physical Regulation in Biology and Medicine, The European Bioelectromagnetics Association; 30(2); pp. 92-99; Doi: 10.1002/bem.20451; Feb. 2009.

Jauchem et al.; Lack of effects on heart rate and blood pressure in ketamine-anesthetized rats briefly exposed to ultra-wideband electromagnetic pulses; IEEE Transactions on Biomedical Engineering; 46(1); pp. 117-120; DOI: 10.1109/10.736767; Jan. 1999.

Jauchem; Ultra-wideband electromagnetic pulses: lack of effects on heart rate and blood pressure during two-minute exposures of rats; Bioelectromagnetics: Journal of the Bioelectromagnetics Society, The Society for Physical Regulation in Biology and Medicine, The European Bioelectromagnetics Association; 19(5):pp. 330-333; Dec. 6, 1998.

Jiang et al.; Frequency-dependent interaction of ultrashort E-fields with nociceptor membranes and proteins; Bioelectromagnetics; 32 (2); pp. 148-163; Feb. 2011.

Jun; Ultrasound as a noninvasive neuromodulation tool; Biomedical Engineering Letters; 2(1); pp. 8-12, DOI: 10.1007/s13534-012-0050-2; Mar. 1, 2012.

Kiranyaz et al.; Multidimensional Particle Swarm Optimization for Machine Learning and Pattern Recognition, Chapter 2: Optimization Techniques; Berlin: Springer; pp. 13-44; (year of pub. sufficiently earlier than effective US filing date and any foreign priority date) 2014.

Kumar et al.; A hyperband antenna to launch and focus fast high-voltage pulses onto biological targets; IEEE Transactions on Microwave Theory and Techniques; 59(4); pp. 1090-1101; DOI: 10.1109/TMTT.2011.2114110; Apr. 2011.

Lazebnik et al.; A large-scale study of ultrawideband microwave dielectric properties of normal, benign and malignant breast tissues obtained from cancer surgeries; Physisc in Medicine and Biology; 52(20); pp. 6093-6115; Oct. 1, 2007.

Lin et al.; Computational methods for predicting field intensity and temperature change; Handbook of Biological Effects of Electromagnetic Fields: Bioengineering and Biophysical Aspects of Electromagnetic Fields; , 3rd Edition, Edited by F.S. Barnes and B. Greenbaum; CRC press; pp. 294-368; (year of pub. sufficiently earlier than effective US filing date and any foreign priority date) 2007.

Miller et al.; Ultrawideband radiation and pentylenetetrazol-induced convulsions of rats. Bioelectromagnetics: Journal of the Bioelectromagnetics Society, The Society for Physical Regulation in Biology and Medicine, The European Bioelectromagnetics Association; 20(5); pp. 327-329; (year of pub. sufficiently earlier than effective US filing date and any foreign priority date) 1999.

Nene et al; Nociceptor activation and damage by pulsed E-fields; Proceedings of SPIE 6219, Enabling Technologies and Design of Nonlethal Weapons; vol. 621904; DOI: 10.1117/12.665181; 13 pages; Downloaded Mar. 15, 2019 from the internet (https://www.spiedigitallibrary.org/conference-proceedings-of-spie) May 26, 2006.

Pakhomova, Ultra-wide band electromagnetic radiation does not affect UV-induced recombination and mutagenesis in yeast; Bioelectromagnetics: Journal of the Bioelectromagnetics Society, The Society for Physical Regulation in Biology and Medicine, The European Bioelectromagnetics Association; 19(2); pp. 128-130; DOI: 10.1002/(SICI)1521-186X(1998)19:2<128::AID-BEM12>3.0.CO;2-M; Dec. 6, 1998.

Petrella et al.; A dielectric rod antenna for picosecond pulse stimulation of neurological tissue, IEEE Transactions of Plasma Science; 44(4): pp. 708-714; DOI: 10.1109/TPS.2016.2537213; Apr. 2016.

Petrella; Non-Invasive Picosecond Pulse System for Electrostimulation; Doctor of Philosophy (PhD); dissertation; Electrical and Computer Engineering; Old Dominion University, DOI: 10.25777/ystf-ry94; May 2018.

Pham et al.; Intelligent Optimisation Techniques: Genetic Algorithms, Tabu Search, Simulated Allealing and Meural Networks; Springer, London; 308 pages; 2000.

Rogers et al.; Strength-duration curve for an electrically excitable tissue extended down to near 1 nanosecond; IEEE Transactions on Plasma Science; 32(4); pp. 1587-1599; Aug. 2004.

Rudiak et al.; Finding the depth of magnetic brain stimulation: a re-evaluation; Electroencephalography and Clinical Neurophysiology/Evoked Potentials Section; 93(5): pp. 358-371; Oct. 1, 1994.

(56) References Cited

OTHER PUBLICATIONS

Ruzgys et al.; Nanosecond range electric pulse application as a non-viral gene delivery method: proof of concept; Scientific Reports; 8(1); pp. 15502; 8 pages; DOI:10.1038/s41598-018-33912-y; Oct. 19, 2018.
Semenov et al.; Excitation and injury of adult ventricular cardiomyocytes by nano- to millisecond electric shocks; Scientific Reports; 8(1); pp. 8233; 12 pages; DOI:10.1038/s41598-018-26521-2; May 29, 2018.
Sherry et al.; Lack of behavioral effects in nonhuman primates after exposure to ultrawideband electromagnetic radiation in the microwave frequency range; Radiation Research; 143(1); pp. 93-97; Jul. 1, 1995.
Vitek et al.; Intraoperative neurophysiology in DBS for dystonia; Movement Disorders; 26{S1); pp. S35-S40; DOI: 10.1002/mds.23619; Jun. 2011.
Voroslakos et al.; Direct effects of transcranial electric stimulation on brain circuits in rats and humans; Nature Communications; 9(483); DOI: 10.1038/s41467-018-02928-3; 40 pages; Feb. 2, 2018.
Walters et al.; No detectable bioeffects following acute exposure to high peak power ultra-wide band electromagnetic radiation in rats; Aviation Space, and Environmental Medicine; 66(6); pp. 562-567; Jun. 1995.
Xiao et al.; A reflector antenna for focusing subnanosecond pulses in the near field; IEEE Antennas and Wireless Propagation Letters; vol. 9, pp. 12-15; DOI: 10.1109/LAWP.2010.2041027; Jan. 22, 2010.
Zhang et al.; Optogenetic interrogation of neural circuits: technology for probing mammalian brain structures; Nature Protocols; 5(3); pp. 439-456; Mar. 2010.

\* cited by examiner

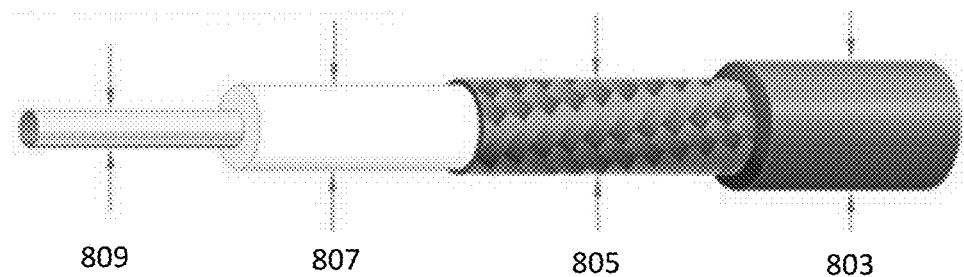
809  807  805  803
FIG. 8
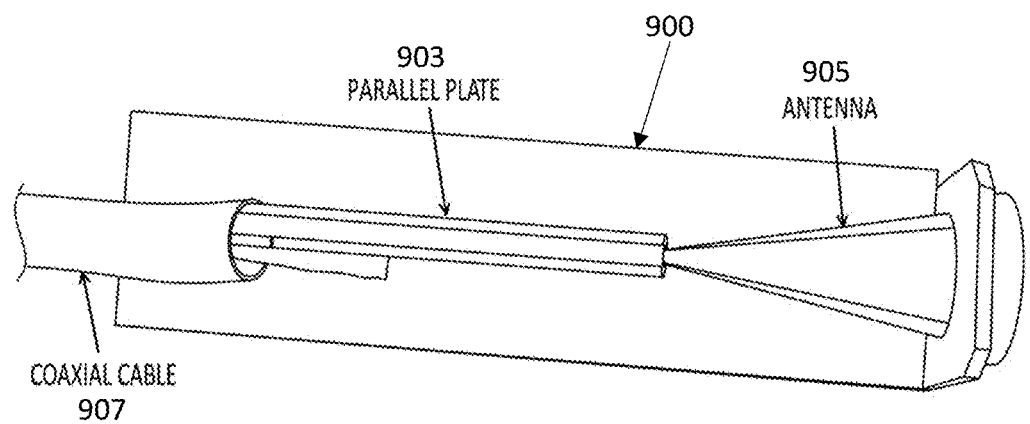
FIG. 9
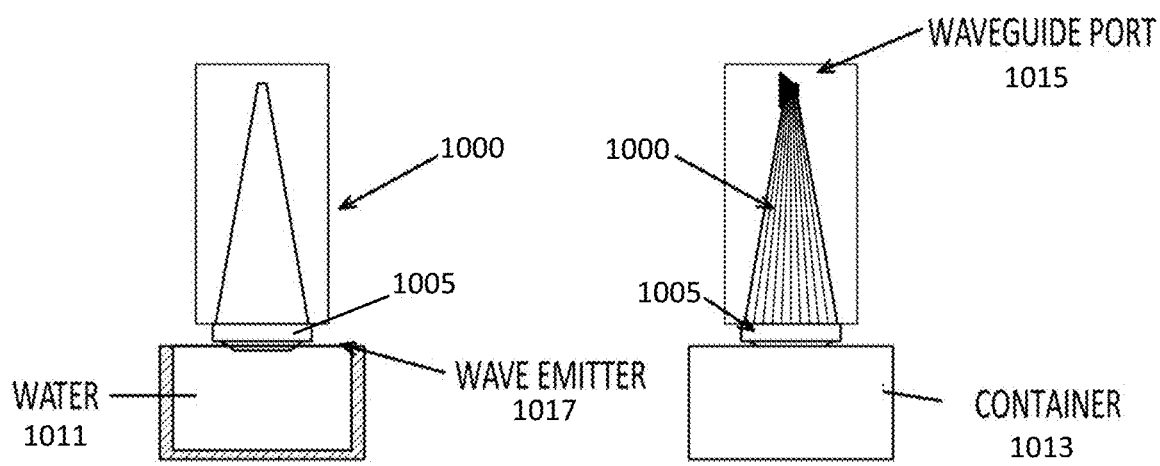
FIG. 10  FIG. 11

| PROBES DISTANCE(MM) | ELECTRIC FIELD INTENSITY(V/M) IN WATER | ELECTRIC FIELD INTENSITY(V/M) IN OIL | PERCENTAGE DIFFERENCES (%) |
|---|---|---|---|
| 1 | 18.681 | 26.29 | 28.9 |
| 2 | 16.811 | 24.126 | 30.31 |
| 3 | 15.048 | 22.167 | 32.11 |
| 4 | 13.493 | 20.283 | 33.47 |
| 5 | 12.132 | 18.492 | 34.39 |
| 10 | 7.89 | 12.583 | 37.29 |
| 20 | 5.44 | 7.40 | 26.34 |

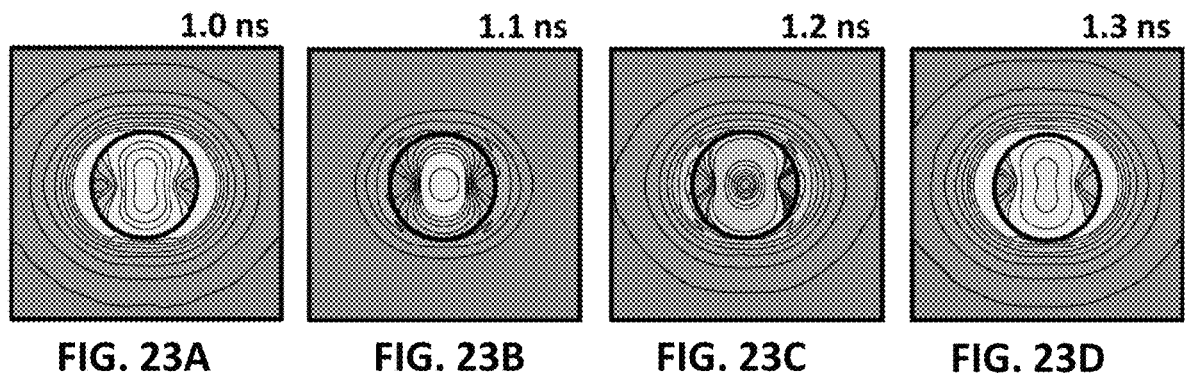
FIG. 23A    FIG. 23B    FIG. 23C    FIG. 23D
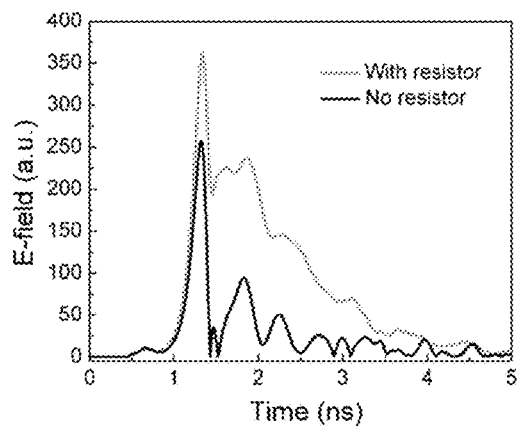
FIG. 24A
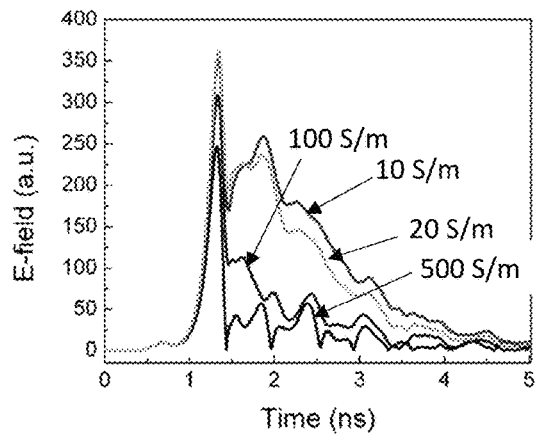
FIG. 24B

FIG. 25A
FIG. 25B
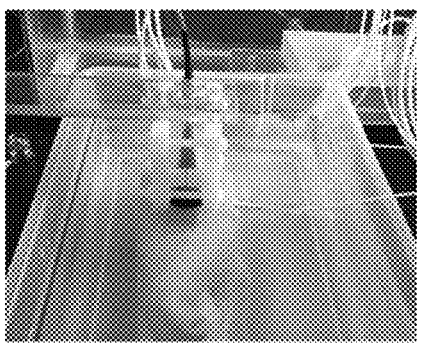
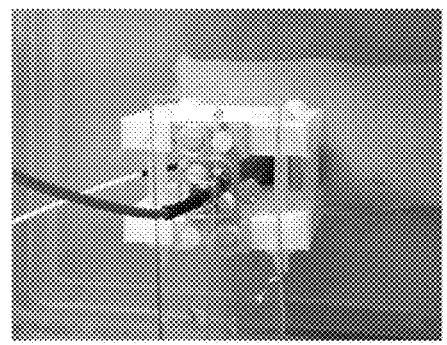
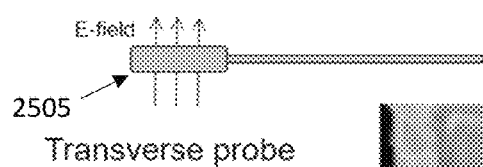
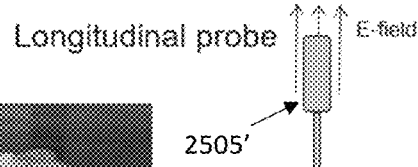
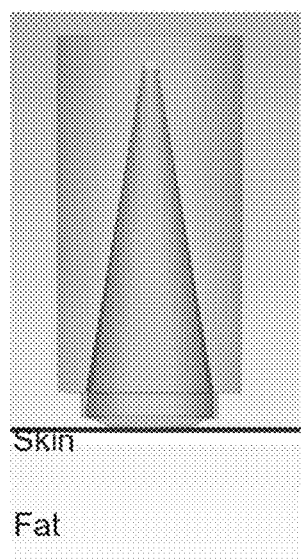
FIG. 25C
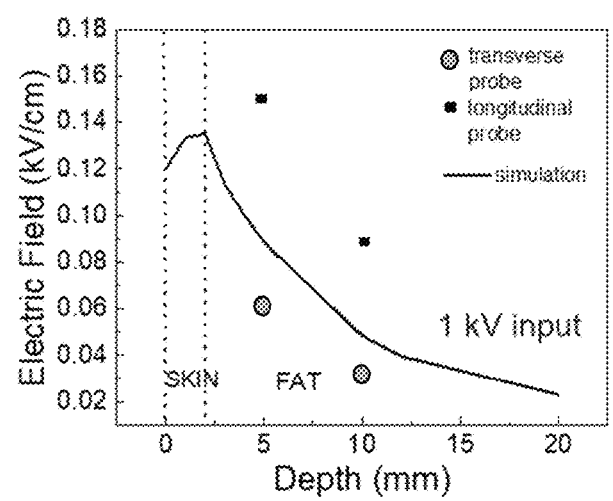
FIG. 26
FIG. 27

RESISTIVELY LOADED DIELECTRIC BICONICAL ANTENNAS FOR NON-INVASIVE TREATMENT

STATEMENT AS TO FEDERALLY SPONSORED RESEARCH

This invention was made with Government support under Grant No. FA9550-15-1-0517 awarded by Air Force Office of Scientific Research. The Government has certain rights in the invention.

CROSS REFERENCE TO RELATED APPLICATIONS

None.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present disclosure relates to apparatuses and methods for treatment of biological tissues using sub-microsecond electric pulses.

BACKGROUND

There are numerous uses for electrical treatment of living tissue using pulses in the nanosecond and picosecond range in medicine, research, and biotechnology. Such applications may include electrostimulation and activation of cells and tissues, induction of cell differentiation and death, tumor and tissue ablation, defibrillation, and the like. Typically, treatments using electrical pulses in the nanosecond and picosecond range use high voltages to exceed the local electric field threshold for desired bio-effects. For example, depending on the desired biological effect, the threshold for single nanosecond pulses may be on the order of several kV/cm for a single pulse, which may be larger for shorter pulses.

The application of electrical energy, particularly at shorter (e.g., sub-nanosecond) pulse widths, has been increasingly used as a therapy in areas where conventional pharmacological approaches become ineffective, including cancer therapies, dermal treatments, treating refractory pain, etc. Different tissues and/or locations may be stimulated. However, most such electrical stimulation methods are invasive and rely on electrodes that are inserted or implanted into the stimulated structure, which may cause complications such as infection, lead migration, and hardware malfunction, as well as potentially damaging the target and surrounding tissues.

Sub-microsecond pulsing (including in the nanosecond or picosecond range), particularly at high-power electric fields is a useful electric stimulus. For example, when using sub-microsecond pulsing, an electric field on the order of 20 kV/cm can activate action potentials on neurons when pulses are applied at a repetition rate of 500 Hz. Higher fields, such as 190 kV/cm, can depolarize a cell membrane. A single pulse of similar field can significantly increase the cytosolic free $Ca^{+2}$ (an important cell signaling molecule). There are also indications that picosecond pulses can cause structural changes of macromolecules.

Because of the short pulse duration, picosecond pulses can be radiated by broadband antennas, allowing for non-intrusive stimulation. Previous antenna design has focused on prolate spheroid impulse radiating antennas (IRAs). Although such antennas have benefit of focusing deeply-situated targets, there are difficulties with implementing them, including large antenna size and large reflection loss at the air-tissue interface, which make the use of IRA impractical.

It would be very useful to access biological targets (including within 0.1-2 cm in depth) to achieve effective electric field level in a non-penetrating manner (e.g., without requiring penetrating electrodes). Unfortunately, it has proven exceptionally difficult to achieve deep, high-power indirect penetration of tissue in the picosecond range, as the power actually delivered to the tissue typically falls off very quickly (within a few millimeters) and increasing the applied power has failed to result in sufficiently higher power at deeper depths.

Described herein are apparatuses and methods that may address these issues.

SUMMARY OF THE DISCLOSURE

The present disclosure relates to antenna apparatuses, such as resistively loaded dielectric biconical antenna apparatuses, that may be used for the application of electromagnetic energy to a biological tissue, including to a human patient. The apparatuses, including systems and devices, described herein may be used to deliver very short pulses (nanosecond and/or sub-nanosecond, e.g., picosecond pulses) to depths of between about 0.1 cm and 5 cm (e.g., between 0.1 cm and 3 cm, between about 0.2 cm and 2 cm, etc.). The energy of the applied electromagnetic field may be sufficient to evoke changes in the tissue to produce biological effects. In some variations, these method may also generate local heating of the regions of applied energy within the tissue. The heat may be generated by applying pulses at a high repetition rate, as demonstrated by examples of nanosecond pulsed experiments.

For example, described herein are resistively loaded antenna systems. These antenna systems may be resistively loaded dielectric biconical antenna systems. For example a resistively loaded antenna system may include: a proximal wave-launching section comprising a cone of dielectric material and one or more pairs of conducive plates (e.g., triangular conductive plates) extending over a portion of the cone of dielectric material; a waveguide (e.g., a cylindrical waveguide) extending distally from a base of the cone of dielectric material; a distal wave-emitting section coupled to the waveguide; and a resistor ring electrically connecting the one or more pairs of conductive plates and extending laterally at least partially around the distal wave-emitting section.

The conductive plates are generally on opposite sides of the proximal wave-launching section (e.g., the cone of dielectric material) and may be, for example, triangular conductive plates. In any of these variations, the conductive plates may have rounded edges.

The dielectric material may be, for example, a low-epsilon material or a high-epsilon material. In some cases, the dielectric material has a dielectric constant of between 6 and 10 and a dielectric strength of greater than 1300 V/mil.

The resistor ring may be configured to reduce electrical reflection of nanosecond and sub-nanosecond pulses. For example, the resistor ring may be configured to provide impedance matching to absorb energy so that low frequency energy applied to the proximal end does not get reflected back from the distal wave-emitting section. In some variations, the resistor ring comprises a mixture of a polymeric material and conductive carbon, or comprises a conductive polylactic acid (PLA) and conductive carbon black.

The waveguide may be cylindrical. In general, the waveguide may have a width in a proximal-to-distal direction that is less than 10% of the length of the proximal wave-launching section in the proximal-to-distal direction.

In some variations, the apparatus (e.g., systems and/or devices) includes an oil-filled cover enclosing at least the proximal wave-launching section and the waveguide.

Any of the apparatuses described herein may include feed coupled to a proximal end of the proximal wave-launching section. For example, the feed may be a two or more (e.g., a pair of) parallel plates with a dielectric liner. The systems described herein may include a coaxial cable electrically coupled to the feed. The systems described herein may also include a high-voltage pulse generator configured to couple to the coaxial cable. For example, the pulse generator may be configured to generate a series of pulses having a pulse width of between about 1 ps and 10 ns. The pulse generator may be configured to generate a series of pulses having a magnitude of between about 1 kV and 1 MV.

For example, a resistively loaded antenna system (e.g., a resistively loaded dielectric biconical antenna system) may include: a proximal wave-launching section comprising a cone of dielectric material and one or more pairs of conducive plates extending over a portion of the cone of dielectric material; a cylindrical waveguide extending distally from a base of the cone of dielectric material, wherein the cylindrical waveguide has a width in a proximal-to-distal direction that is less than 10% of the length of the proximal wave-launching section in the proximal-to-distal direction; distal wave-emitting conical section coupled to the cylindrical waveguide; and a resistor ring electrically connecting the one or more pairs of triangular conductive plates and extending laterally around the distal wave-emitting conical section.

Also described herein are methods for treating a patients and/or a biological tissue using any of the apparatuses described herein. For example a method of treating a biological tissue may include: placing a distal wave-emitting section of the resistively loaded antenna against a tissue; applying a plurality of sub-microsecond pulses from a pulse generator to one or more pairs of conducive plates extending over a proximal section of the resistively loaded antenna, wherein the one or more pairs of conductive plates are electrically connected through a resistor ring configured to prevent or limit reflection of electrical energy back towards the pulse generator; and delivering the sub-microsecond waves of electrical energy to the tissue in a region that is focused between 0.1 and 5 cm from a distal end of the resistively loaded antenna.

A method for treating a patient may include: coupling a resistively loaded dielectric biconical antenna to a pulse generator, so that a proximal end of the resistively loaded dielectric biconical antenna is electrically coupled to the pulse generator; placing a distal wave-emitting conical section of the resistively loaded dielectric biconical antenna against a tissue; applying a plurality of sub-nanosecond pulses to the resistively loaded dielectric biconical antenna so that the energy is applied to one or more pairs of triangular conducive plates separately extending over a portion of a cone of dielectric material at the proximal end of the resistively loaded dielectric biconical antenna; causing emission of sub-nanosecond waves of electrical energy from a distal wave-emitting conical section of the resistively loaded dielectric biconical antenna; and preventing or limiting reflection of electrical energy back towards the pulse generator by electrically connecting each of the triangular conductive plates of the one or more pairs of triangular conductive plates through a resistor ring arranged laterally over the distal wave-emitting conical section of the resistively loaded dielectric biconical antenna, delivering the sub-nanosecond waves of electrical energy to a tissue region that is focused between 0.1 and 5 cm from the distal end of the resistively loaded dielectric biconical antenna.

The method may include coupling the resistively loaded antenna (e.g., a resistively loaded dielectric biconical antenna) to pulse generator, e.g., to a feed that comprises a pair of parallel plates with a dielectric liner.

Applying may comprise applying the plurality of sub-nanosecond pulses from a proximal wave-launching section of the resistively loaded dielectric biconical antenna comprising the one or more pairs of (e.g., triangular) conductive plates and the cone of dielectric material so that passing the plurality of sub-microsecond pulses through a cylindrical waveguide extending distally from a base of the proximal section and into the distal wave-emitting section.

In some variations, the waveguide (which may be, but is not limited to a cylindrical waveguide) has a width in a proximal-to-distal direction that is less than 10% of the length of the proximal wave-launching section in the proximal-to-distal direction.

In any of these variations, emitting may comprise radiating faster portions of the sub-nanosecond waves from the distal wave-emitting conical section of the resistively loaded dielectric biconical antenna. Applying a plurality of sub-microsecond (or sub-nanosecond, e.g., picosecond) pulses may comprise applying a train of pulses having a magnitude of between about 1 kV and 1 MV. For example, applying the plurality of sub-microsecond (e.g., sub-nanosecond, e.g., picosecond) pulses may comprise applying a train of sub-nanosecond pulses having a frequency of between 1 Hz and 1 GHz.

Any of these methods may also include delivering microsecond or millisecond pulses through the resistor ring to the tissue.

Also described herein are method of operating any of the resistively loaded antenna apparatuses described herein. For example, described herein are methods of operating a system (e.g., operating a resistively loaded antenna or a resistively loaded biconical antenna apparatus) that may include: applying a plurality of sub-microsecond (e.g., sub-nanosecond, e.g., picosecond) pulses from a pulse generator to one or more pairs of conducive plates, e.g., extending over a proximal section of the resistively loaded antenna, wherein the one or more pairs of conductive plates, which may be triangular conductive plates, that are electrically connected through a resistor ring configured to prevent or limit reflection of electrical energy back towards the pulse generator; and emitting, from a distal wave-emitting section of the antenna, the sub-microsecond waves of electrical energy so that the emitted energy is focused between 0.1 and 5 cm from the distal end of the resistively loaded antenna.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative embodiments, in which the principles of the disclosure are utilized, and the accompanying drawings of which:

FIG. 8 is an example of a coaxial cable that may be used to connect a resistively loaded dielectric biconical antenna to a pulse generator.

FIG. 9 is an example of an assembled prototype of a resistively loaded dielectric biconical antenna coupled to a parallel plate feed and through the feed to a coaxial cable; this assembly may be used to apply energy (e.g., submicrosecond, nanosecond and/or sub-nanosecond pulsed energy) to a tissue non-invasively.

FIG. 10 schematically illustrates a section through an antenna of the present disclosure and a container holding water that is used to simulate the operation of the antenna applying energy to a biological tissue.

FIG. 11 shows an external view of the setup of FIG. 10, which may be used to test the properties of the antenna.

FIGS. 23A-23D show simulated electrical fields produced by a resistively loaded dielectric biconical antenna in water at different times (respectively: 1.0 ns, 1.1 ns, 1.2 ns, and 1.3 ns), resulting in a focal point within the target region.

FIG. 24A is a graph showing the effect of the resistor ring on a resistively loaded dielectric biconical antenna.

FIG. 24B shows the e-field produced by various conductance values for the resistor ring of a resistively loaded dielectric biconical antenna.

FIGS. 25A-25C illustrate one example of an experimental set-up for testing a resistively loaded dielectric biconical antenna in tissue (e.g., porcine tissue), including measuring transverse and longitudinal electric fields within the tissue when applying very short pulses (e.g., picosecond pulses) into the tissue using the resistively loaded dielectric biconical antenna. FIG. 25A shows the water bath with the tissue and a resistively loaded dielectric biconical antenna placed against the tissue in the bath. FIG. 25B is a top view of the resistively loaded dielectric biconical antenna applicator. FIG. 25C is a view through the tissue showing the dimensions of the tissue. The probes (transverse probe and longitudinal probe) are also schematically illustrated.

FIG. 26 is a schematic drawing showing the placement of a resistively loaded dielectric biconical antenna on a skin surface.

FIG. 27 is a graph showing the produced electric field from a resistively loaded dielectric biconical antenna at different depths into the tissue as measured by a setup as shown in FIGS. 25A-25C and compared to simulated values.

DETAILED DESCRIPTION

Figure 1A:
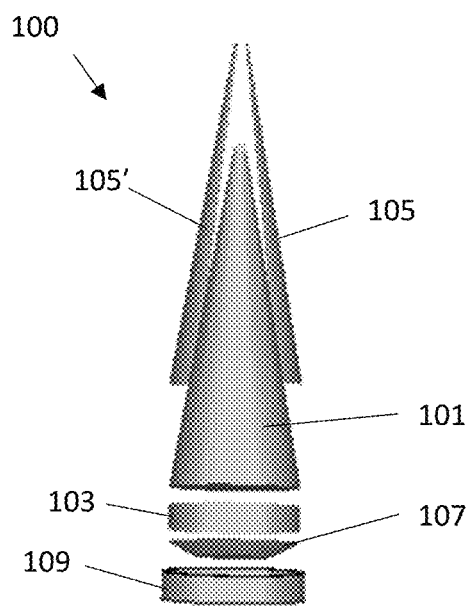
FIG. 1A is an exploded view of one variation of a resistively loaded dielectric biconical antenna as described herein.

Described herein are resistively loaded dielectric biconical antenna apparatuses, including systems and devices, that may be used to transmit very short electrical pulses (e.g., nanosecond, sub-nanosecond, picosecond, etc.) into tissue at a depth of at least 2 cm at energy levels sufficient to invoke biological changes in the tissue. These apparatuses may also be applicators or may be included as part of an applicator assembly for the delivery of pulsed electrical energy, and in particular, may form part of a system for the delivery of very short electrical pulses to tissue. In some variations these antenna/applicator apparatuses may be referred to as picosecond pulsed antennas (PPAs), or as resistively loaded dielectric biconical antennas. In general, these apparatuses (e.g., devices and systems) may be used to perform methods of treating tissue non-invasively, e.g., without penetrating the tissue to be treated.

The resistively loaded dielectric biconical antennas described herein are particularly effective at transmitting very short (e.g., sub-microsecond, including nanosecond, sub-nanosecond, picosecond) pulses, although in some variations, longer pulses (e.g., microsecond or millisecond pulses) may be used.

In general, the resistively loaded dielectric biconical antennas described herein may include a shape that includes a dielectric cone that may be partially, but not completely clad by one or more pairs of (e.g., triangular) conductive plates bent around and extending distally down the dielectric cone, a cylindrical region at the base of the dielectric cone, and a conical wave-emitting distal region at the distal end of the apparatus. A resistor ring structure or resistor ring is positioned around the conical wave-emitting distal region. As described in more detail below, the resistor ring may reduce reflections of the energy pulses and may also makes contact with the tissue surface to provide a path for longer pulses. The apparatuses described herein may be referred to as "resistively loaded" to indicate that the conductive antenna plates extending along the outside of the proximal dielectric cone are connected to a resistor ring that encircles at least part of the lateral sides of the distal conical wave-emitting section and dramatically improves the function of the resistively loaded dielectric biconical antenna apparatuses described herein.

The resistor ring structure connect the one or more pairs of conductive plates on the dielectric cone structure and provides impedance matching to absorb energy so that low frequency energy does not get reflected back to the generator, which may connect to the tip of the dielectric cone. The resistor ring may both protect from overvoltage of the pulse generator, but may also permit the antenna to deliver the pulses more deeply within the tissue and prevent energy loss. Thus, even very short, e.g., nanosecond and/or picosecond, pulses may be applied into the target tissue to a depth of greater than about 1-2 cm. The resistor ring may have a value that allows passage of higher frequency energy, while lower frequency components may have been selectively attenuated. Low frequency components may be passed depending on the resistivity of the resistor ring, particularly when compared to the resistance of the subjects (e.g., patient's) skin. Thus, in general, the antenna apparatuses described herein may be placed in contact with the patient's tissue during use (e.g., against the skin, in some variations), to project the therapeutic energy into the tissue at a depth of 1-2 cm or more. Typically, therapeutic energy having very short (e.g., nanosecond, sub-nanosecond, picosecond, etc. duration component) pulses can focus the delivery of energy in a depth of tissue, allowing relatively small spot sizes; longer pulses (e.g., microsecond, millisecond duration components) can help alleviate the discomfort at the tissue, including at the skin surface. Within the tissue, including at the target depths, the longer duration pulses are more greatly attenuated, while shorter pulses may not be as attenuated.

The resistor rings described herein may be formed of any appropriate material having the desired electrical properties described herein. For example, in some variations, the resistor rings may be formed of a carbon-based plastic material, including but not limited to a mixture of nanotubing plastic (e.g., conductive carbon particles). The geometry of the ring may be configured so that that there is an imperfect match between the characteristic impedance of the antenna and the target. This may allow a leak current to reach the tissue surface (e.g., skin) through the resistor. Thus, the resistor ring may have an impedance that is not the same as the antenna.

Thus, in general, the methods an apparatuses described herein may be used to apply energy into the tissue from a tissue surface to a depth of about 1-2 cm or greater.

Figure 1B:
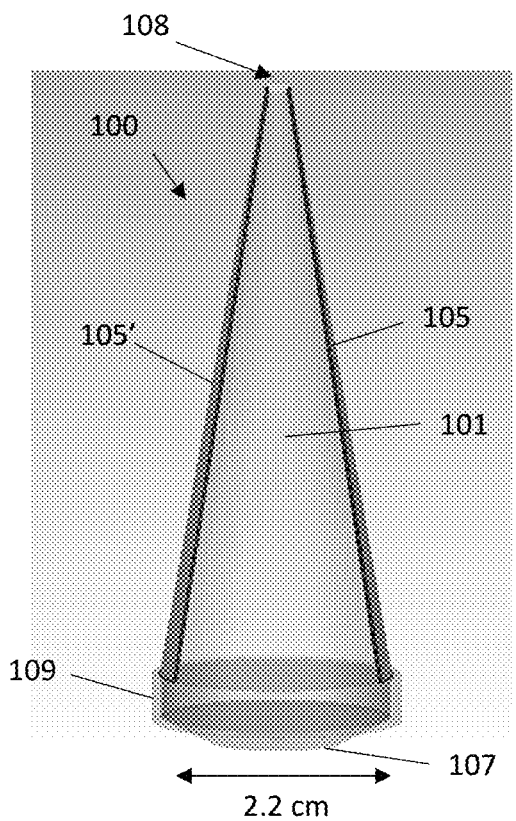
FIG. 1B is a front view of the antenna of FIG. 1A.
Figure 1C:
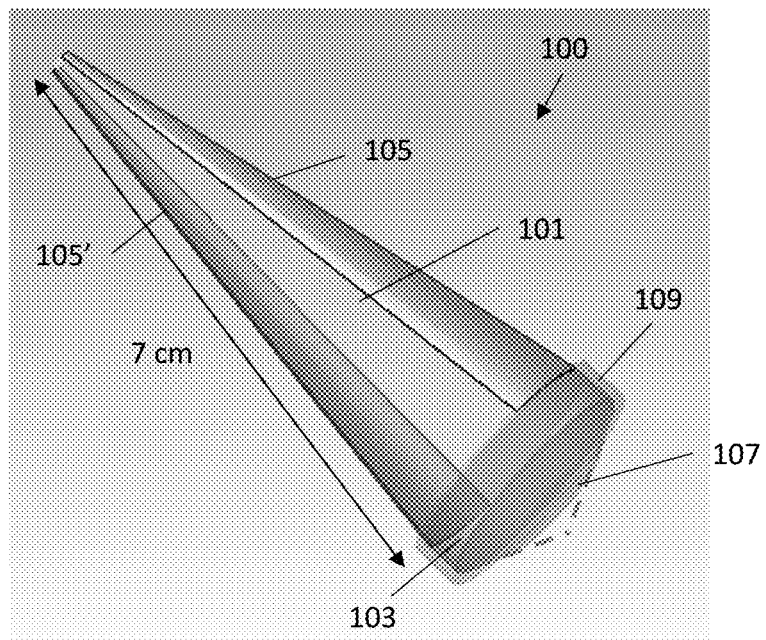
FIG. 1C is a side perspective view of the antenna of FIG. 1A.
Figure 6:
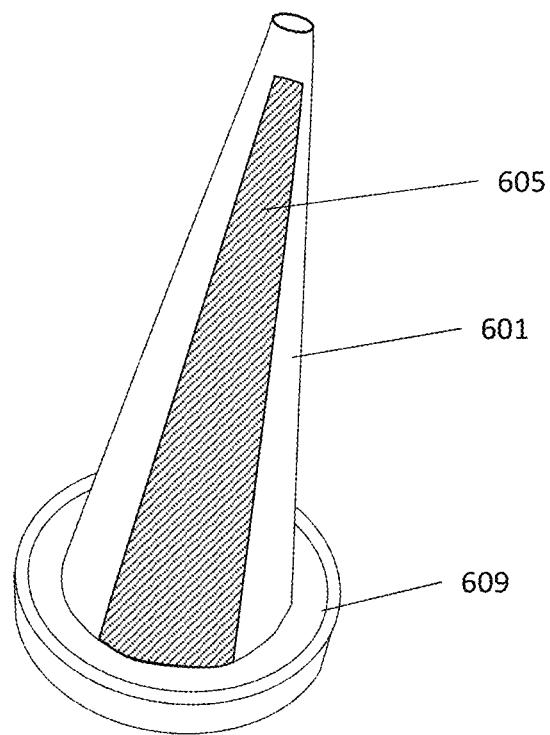
FIG. 6 is a perspective view of an example of a prototype resistively loaded dielectric biconical antenna.

FIGS. 1A-1C show an example of a resistively loaded dielectric biconical antenna 100. FIG. 1A is a schematic exploded view of one example of an applicator/antenna apparatus showing five portions or sections. The proximal section 101 (which may connect to a pulse generator at the proximal tip) is the wave-launching section that is a dielectric cone having a high dielectric constant. The base (end plate at the distal end) of the dielectric cone is coupled (directly or in indirectly) to, or continuous with, a dielectric waveguide, such as a cylindrical dielectric waveguide 103 of FIG. 1A. The distal end of the apparatus is a wave emitting section 107 that is in the example of FIG. 1A also approximately conical. A V-shaped set of conductive plates 105, 105' forms the antenna portion that at least partially wraps around the dielectric cone and extends down the length of the dielectric cone 101. A resistor ring 109 is positioned around the region between the cylindrical dielectric waveguide 103 and the inverted conical wave-emitting section 107. An example of an assembled applicator/antenna apparatus is shown in FIG. 6 and described below.

In the exemplary apparatus shown, the dielectric cone 101 and the antenna plates (e.g., the pair of electrically conductive plates 105, 105' wrapped partially around the cone), may launch waves. In FIG. 1A, the conductive plates are formed of two triangular conductive plates that are bent in a conical shape to cover the cone. Because the plates have a finite length, the antenna may act like a small aperture antenna, having a finite bandwidth.

The dielectric waveguide 103 may be formed of a dielectric rod allowing the electromagnetic waves to travel from the wave launching section to the emitting section (e.g., the conical wave-emitting section 107). A hybrid wave that has both transverse electric and magnetic components may be established in this section, which may radiate the electric field into either a free space or a target. The conical shape of this emitting section 107 may allow it to act as a convex lens which confines the electric field to a small area, so that a good spatial resolution can be achieved inside the target.

The resistor ring 109 may be added to the end of the conductive plates and may reduce or eliminate low-frequency waves bouncing back towards the pulse generator to protect the pulse generator. In some example, the resistor ring is formed of a conductive polylactic acid (PLA) which includes a dispersant and conductive carbon black. In at least some of the examples described herein, the resistor ring was modeled using software and created using a 3D printer. The resistor ring may then be attached (e.g., press-fit) onto the emitting section 107 and/or between the emitting section 107 and the distal end of the dielectric waveguide 103, so the ring connects both conductive plates 105, 105'.

In variations of the resistively loaded dielectric biconical antenna that are configured to be used against skin, the material dielectric constant may be approximately close to that of a skin (e.g., 40). For example, a composite material of MgO and stabilized zirconia (e.g., "TTZ" or DURA-Z) having a reported dielectric constant of about 28 may be used for the dielectric material. Knowing the dielectric constant allows an approximation of the radius of the antenna rod for a given pulse duration:

$$\sqrt{\varepsilon_r} R > t_p c_o \quad [1]$$

In this equation, $t_p$ is the pulse duration, $c_0$ is the speed of light, $\varepsilon_r$ is the relative permittivity, R is the antenna rod radius. This condition means that laterally the boundary from the rod to the air shouldn't cause a strong reflection for most of the pulse. The characteristic impedance of the wave launching section, mainly for the conductive triangular plates, can be calculated using the following equation:

$$2Z_o = \frac{Z_c}{\sqrt{\varepsilon_r}} \frac{k(\cos\phi_0)}{k(\sin\phi_0)} \quad [2]$$

where:

$$k = \int_0^{\frac{\pi}{2}} \frac{d\beta}{\sqrt{1-m(\sin\beta)^2}} \quad [3]$$

From this equation, m is a result of the function $\cos\phi_0$ and $\sin\phi_0$, where $$0 < \phi_0 < \frac{\pi}{2}.$$

Figure 2:
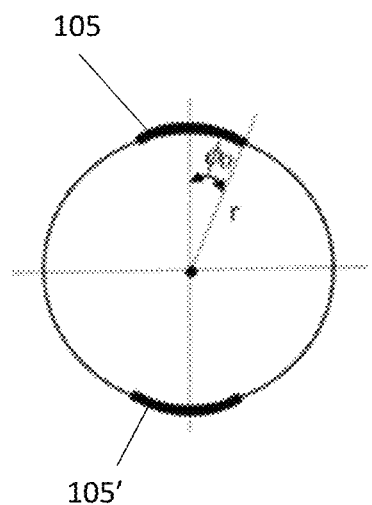
FIG. 2 is a cross-sectional view of an antenna/applicator similar to that shown in FIGS. 1A-1C and FIG. 5.
Figure 3:
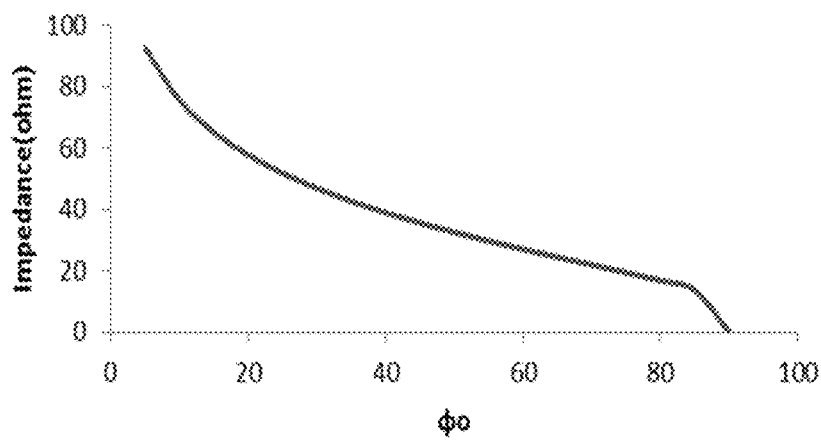
FIG. 3 is a graph illustrating an example of a characteristic impedance of portion of the resistively loaded dielectric biconical antenna formed by the dielectric cone and the pair of electrically conductive (antenna) plates wrapped partially around the proximal dielectric cone.

$Z_c$ is the free space impedance which is equaled to 377 ohms, and $\varepsilon_r$ is the dielectric permittivity of the dielectric material. In case the dielectric constant of TTZ, which is 28. From the equation above, we can map the azimuth angle ($\phi0$), which is correlated to the spread of the PEC (perfect electric conductor) cone of the conductive plates (in some variations, triangular conductive plates). The angle ($\phi_0$) may be calculated using elliptic integral function provided, e.g., by Matlab. FIGS. 2 and 3 show the description of $\phi_0$ and the character impedances of an exemplary TTZ antenna such as the one described above.

FIG. 2 shows a cross-sectional view of a resistively loaded dielectric biconical antenna similar to that shown in FIGS. 1A-1C. The graph in FIG. 3 illustrates one example of a characteristic impedance of the wave launching section 101. In this example, the characteristic impedance is tightly related to the azimuth angle ($\phi_0$), which varies from 0 to 90°. As the angle increase, the impedance decreases. The impedance is infinite when $\phi_0$ is zero and approaching zero when $\phi_0$ is 90° (e.g., short circuit). One desired characteristic impedance is about 50Ω, which makes $\phi_0$ approximately 26.75°.

In some of the apparatuses described herein, the resistively loaded dielectric biconical antenna has a long wave launching section 101 ($l\sqrt{\varepsilon_r}$), which may provide advantages in frequency independence, uniform azimuthal directivity, and TEM mode excitation. In addition, the dielectric waveguide 103 may be short (particularly as compared to the wave launching section). For example, the width of the cylindrical dielectric waveguide 103 in the proximal-to-distal axis may be e.g., less than 15%, 12%, less than 10%, less than 9%, less than 8%, etc. of the length of the wave launching section or dielectric cone region 101 in the proximal-to-distal axis. This may reduce dielectric loss and broadening effects of the pulses travelling back from the wave launching section. The tip of the wave emitting section (e.g., conical wave-emitting section 107) may be flat in order to reduce the leakage loss to the free space.

Figure 4:
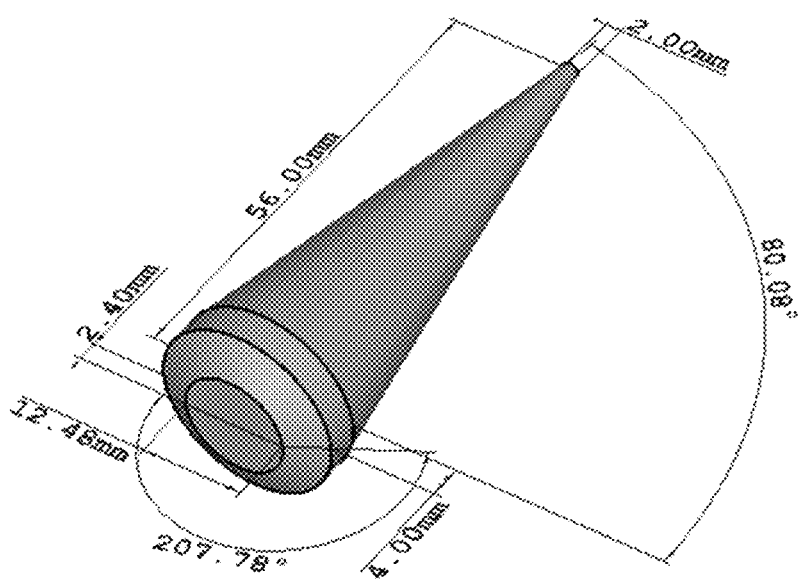
FIG. 4 is a perspective view of one variation of a dielectric cone, cylindrical dielectric waveguide, and distal conical wave-emitting section (without the resistor ring or conductive plates) of the antenna, showing exemplary dimensions.

The antennas/applicators described herein may be constructed in any appropriate manner. In some variations the antenna body may be machined, e.g., using a diamond tip tool to grind the dielectric (e.g., TTZ) material into a desired conical shape. FIG. 4 illustrates one example of a dielectric body of an example of a resistively loaded dielectric biconical antenna as described herein (without the resistor ring or conductive plates attached) showing exemplary dimensions. These dimensions are intended for illustrative purposes and are not intended to be limiting. The relative dimensions may be +/-2%, 5%, 7%, 10%, 15%, 20%, etc. The overall dimensions may be scaled up or down.

Figure 5:
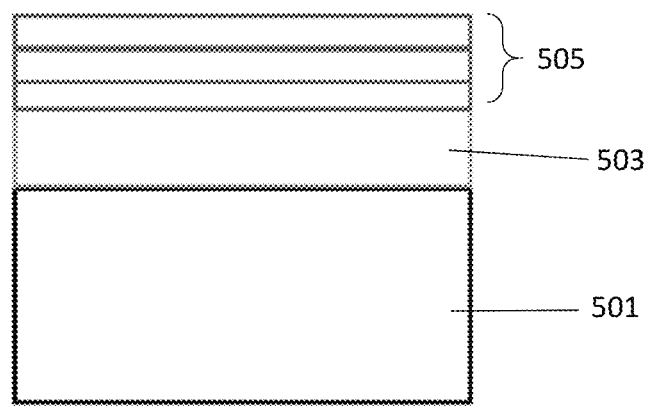
FIG. 5 is a schematic showing a section through a portion of an electrically conductive (antenna) plate formed by layers of conductive paint, such a copper-containing paint, over a proximal dielectric cone.

After the antenna dielectric body was created, the cone section may be prepared for the attachment of, for example, the one or more pairs of triangular, conductive plates. The PEC-dielectric material may be prepared to have a smooth and tight contact. For example, two (e.g., triangular) conductive plates 105, 105' may be first made from a conductive material (e.g., copper tape). The conductive plates may be adhesively attached to the cone region. In some variations, as illustrated in FIG. 5, a conductive paint (e.g., conductive copper paint) may be used. For example, a conductive copper paint may contain tiny copper particles. Two triangular conductive plates may be created by depositing multiple layers 505 of copper paint. A layer of primer 503 may be applied before the deposition, to improve the adhesion of the copper paint to the TTZ material 501. A thin layer of epoxy glue may be used on the plate edges.

FIG. 6 shows one example of a resistively loaded dielectric biconical antenna with a resistor ring 609 attached over a distal conical wave-emitting section (not visible). One of two conductive plates 605 is visible on the outer surface of the proximal dielectric cone region 601.

Figure 7:
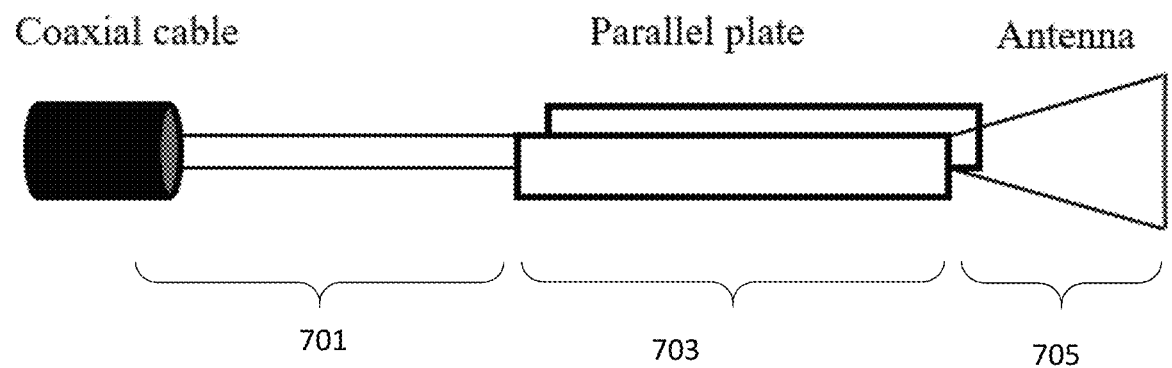
FIG. 7 is a schematic showing a resistively loaded dielectric biconical antenna coupled via a parallel plate feed to a coaxial cable to connect the resistively loaded dielectric biconical antenna to a pulse generator (e.g., a high-voltage pulse generator).

In general, any of the resistively loaded dielectric biconical antenna apparatuses described herein may include a feed connecting it to a pulse generator for delivering pulses to biological targets. The pulse generator is typically a high-voltage pulse generator for delivering pulses to feed into the antenna. Any appropriate feed structure may be used. For example, two parallel plates with a Teflon dielectric liner may be used as a feed structure, because this may provide some space between the plates and can prevent the breakdown at the tip of the antenna when high voltage is applied. Another advantage of this type of feed is it maintains a balance field along the plates. This may aid in a uniform field to the antenna. FIG. 7 illustrates one example of a feed structure including a coaxial cable 701 and a parallel-plate feed 703 coupled to the resistively loaded dielectric biconical antenna 705. In some examples described herein, the coaxial cable connecting the power source to the resistively loaded dielectric biconical antenna may be RG271 cable, similar to that shown schematically in FIG. 8.

In order to connect the coaxial cable to the parallel plates, the jacket 803 of the cable may be removed. The inner 809 and outer 805 conductors of the coaxial cable (separated by insulation 807) may act as the positive and negative terminal which will be then connected to the parallel plates. The impedance of the coaxial cable in this example is approximately 50Ω, which may match the impedance of the plates and the antenna impedance. For a given Teflon sheet that has the thickness of 0.8 cm, in order to determine the dimension of the parallel plates, an impedance formula may be applied:

$$Z_0 = Z_c \left(\frac{d}{w}\right) \sqrt{\frac{\mu_r}{\varepsilon_r}} \quad [4]$$

where $Z_0$ is the parallel plates' impedance, $Z_c$ is the impedance in free space, d is the gap distance, w is the width of the parallel plates, $\mu_r$ is the relative permeability, and $\varepsilon_r$ is the relative permittivity.

In the exemplary device shown in FIG. 9, the gap distance was 0.8 cm, $Z_c$=377 ohms, $Z_0$=50 ohms, $\mu_r$=1 in air, and $\varepsilon_r$=2.1. The width of the parallel plates was determined to be 4.16 cm. In this case, the length and the thickness of the parallel plates are ignored. The parallel-plate structure was held in place with a 3D printed holder 900. The feed structure (including parallel plates 903 and coaxial cable 907) and the antenna 905 were soldered to prevent the impedance discontinuity. Furthermore, in this example, an epoxy glue was applied to stabilize the coaxial cable and the antenna.

Three dimensional (3D) simulations were performed to characterize the resistively loaded dielectric biconical antenna apparatus. The input signal of the simulation was a default Gaussian waveform with the magnitude of 1 V. The antenna was simulated for two different conditions in which the antenna was immersed in water and oil respectively. The choice of water and oil was because they could prevent and suppress high voltage breakdown at the interface between the antenna and air. The electric field was probed at 1 mm, 2 mm, 3 mm, 4 mm, 5 mm, 10 mm, and 20 mm away from the wave emitting section. The two scenarios (shown in FIGS. 10 and 11) were simulated in order to compare with the experimental results and validate the performance of the antenna. In FIG. 10 (showing a section through the antenna and container) and FIG. 11 (showing an external view), the resistively loaded dielectric biconical antenna apparatus 1000 includes a resistor ring 1005. The antenna includes a wave emitter 1017 and a waveguide port 1015 for connecting to a waveguide (e.g. parallel plate waveguide). In FIGS. 10 and 11 the apparatus is connected to a model of biological tissue, a container 1013 filed with water 1011 that may be used to simulate the penetration into the tissue.

Figures 12, 13:
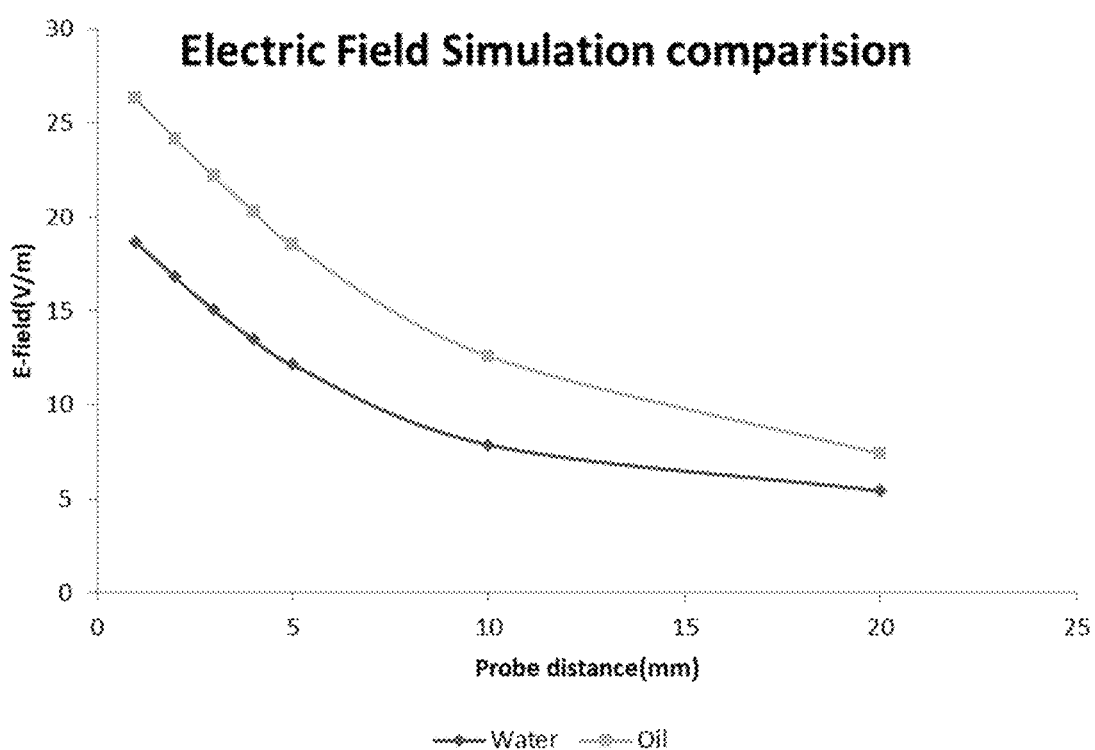
FIG. 12 is a table summarizing the field values at different distances from a resistively loaded antenna such as the one shown in FIGS. 10 and 11.
FIG. 13 is a graph of the simulation data of FIG. 12, showing the electric field simulation in water and oil.
Figures 14A, 14B, 14C:
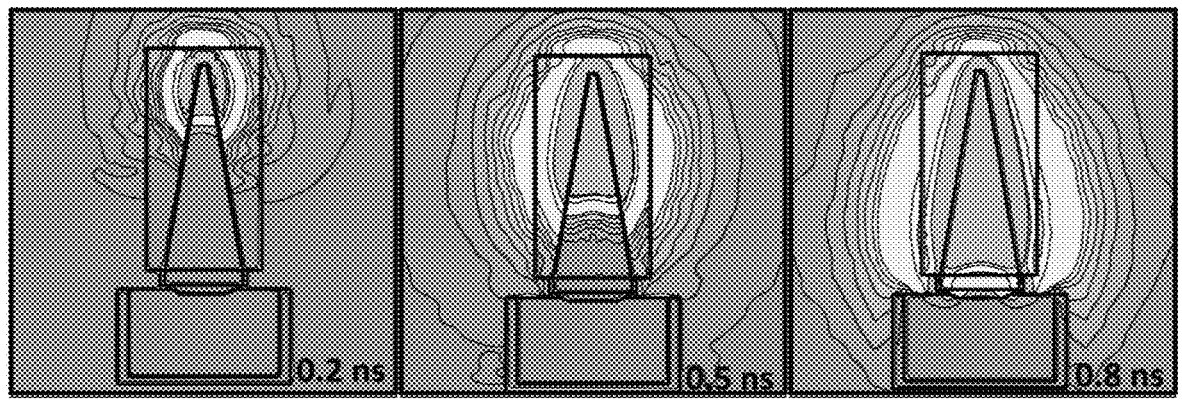
FIGS. 14A-14I show electric field maps, illustrating how the field travels from an antenna source of a resistively loaded dielectric biconical antenna at different times in oil.
Figures 14D, 14E, 14F:
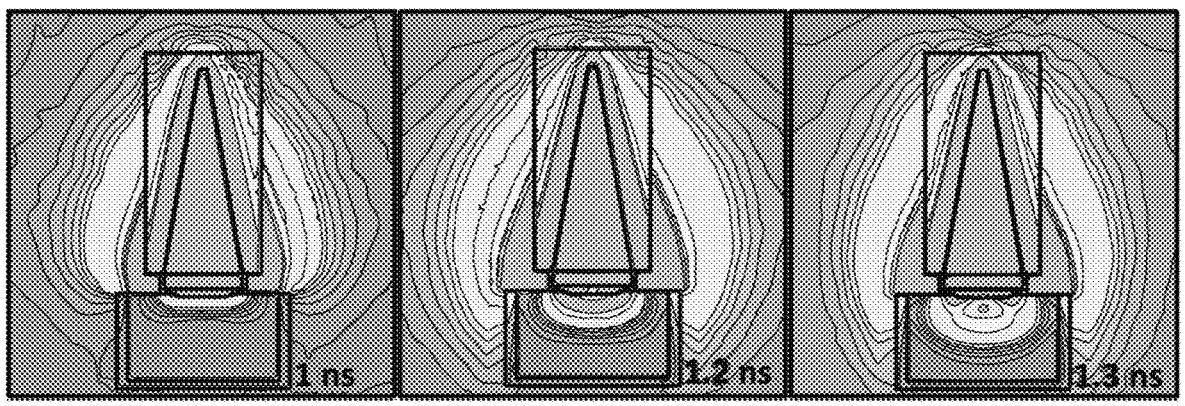
Figures 14G, 14H, 14I:
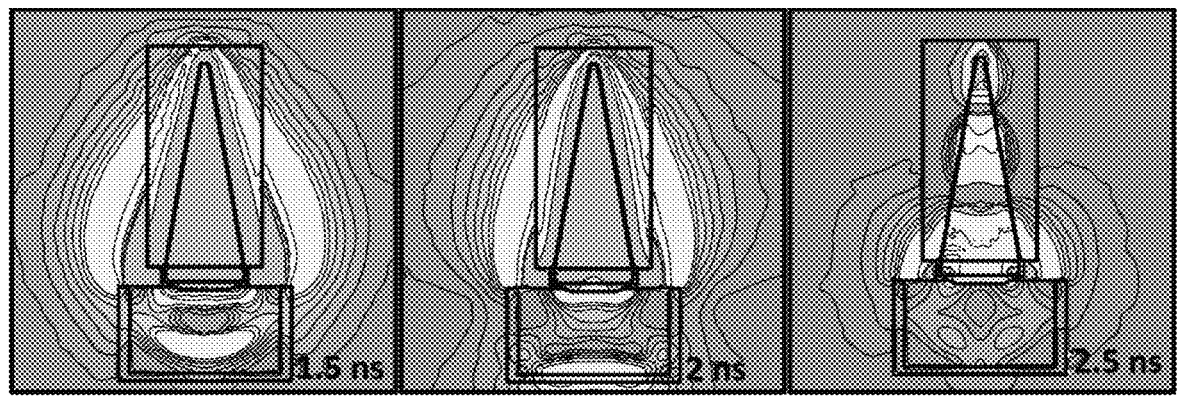
Figure 15A:
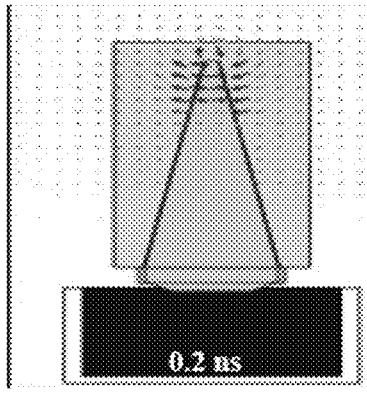
FIGS. 15A-15I showing the direction of the E-field in oil over time (arrow size and length corresponds to relative intensity).
Figure 15B:
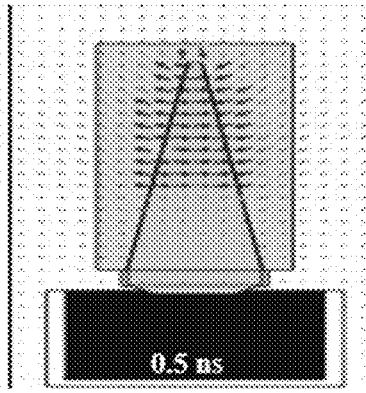
Figure 15C:
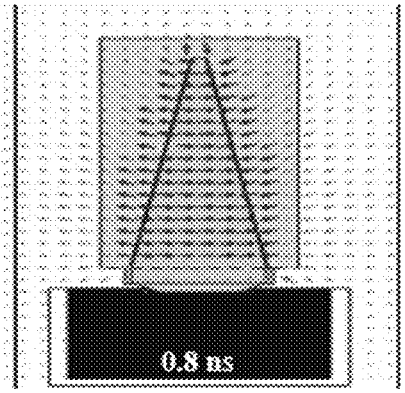
Figure 15D:
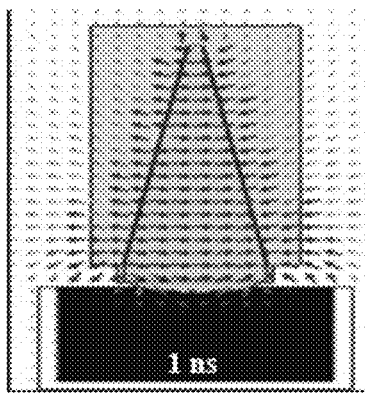
Figure 15E:
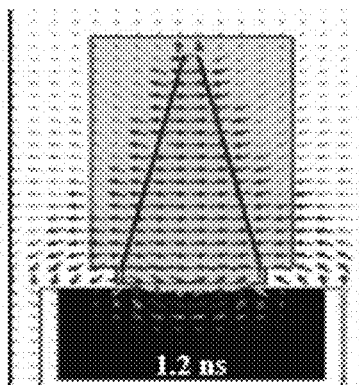
Figure 15F:
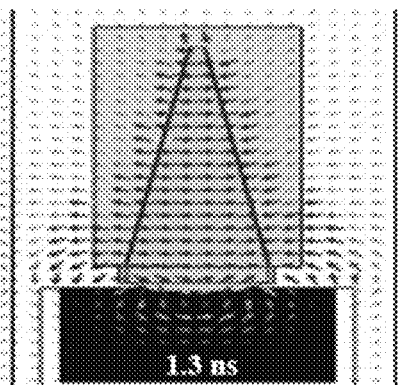
Figure 15G:
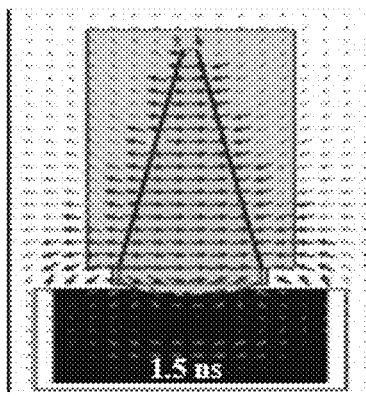
Figure 15H:
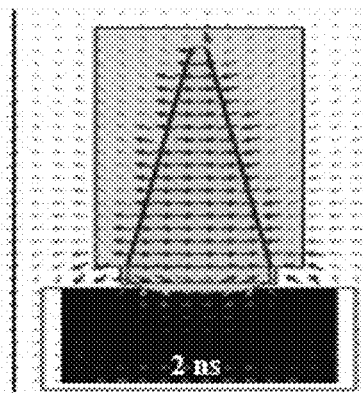
Figure 15I:
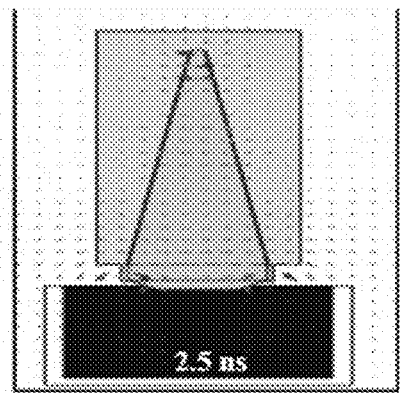
Figure 16A:
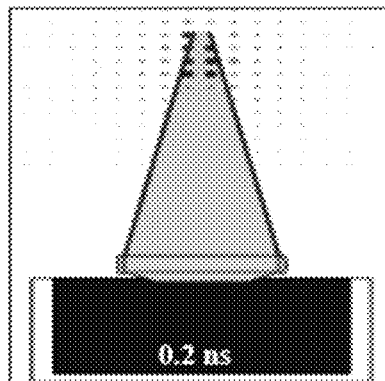
FIGS. 16A-16I show the magnetic field simulation in oil for one variation of the antenna of the present disclosure.
Figure 16B:
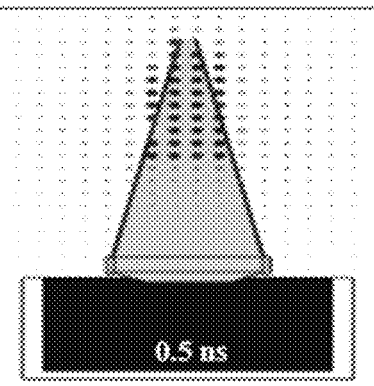
Figure 16C:
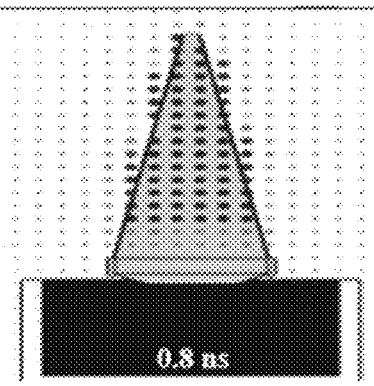
Figure 16D:
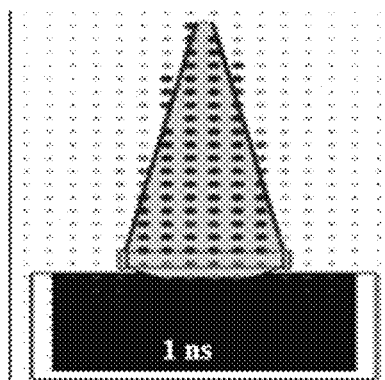
Figure 16E:
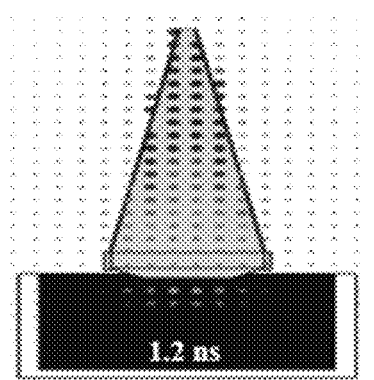
Figure 16F:
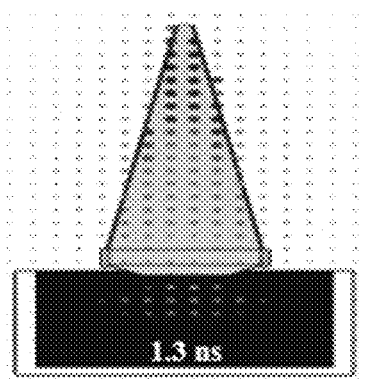
Figure 16G:
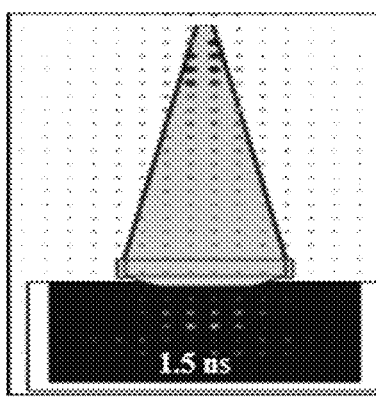
Figure 16H:
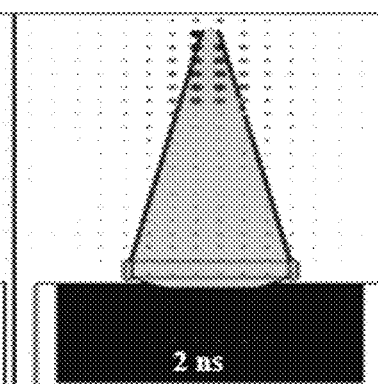
Figure 16I:
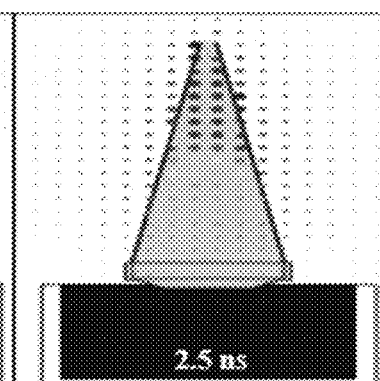

FIG. 12 is a table summarizing the field values at different distances from a resistively loaded dielectric biconical antenna such as the one shown in FIGS. 10 and 11. This simulation data is also shown graphically in FIG. 13, showing the electric field simulation in water and oil. As shown, the electric fields for both conditions show similar characteristics. They have the same decay trend. The field is higher nearer the antenna tip but levels out after 1 cm. The results show that the magnitude of the electric field for the oil case is 31.83% higher than that for water case.

FIGS. 14A-14I show heat maps of the intensity of the electric field, illustrating how the field travels from the antenna source at different times in oil. Before 1 ns (FIGS. 14A-14C), the electric field is mostly guided by the antenna, but there is also a wave that travels faster outside the antenna, which does not contribute to the overall field at the target because it gets dispersed once arriving at the wave emitting section. At 1.5 ns (FIG. 14G), there is a pulse at a depth of approximately 1 cm, which continuously travels deeper but its intensity decreases rapidly.

The electric field direction of the antenna emission is important to the characterization of the antenna and measurement. To investigate the direction of the fields along the antennas structure, simulation results were taken for different time points from 0.2 ns to 2.5 ns. This is illustrated in FIGS. 15A-15I, showing the direction of the E-field in oil over time. In the antenna, the direction of the field is horizontal. The direction remains unchanged even after the wave reaches the emitting section. A closer examination shows that the radiated wave has the same direction as that inside the antenna and it is determined by the original wave port excitation signal.

Another simulation was carried out to determine the direction of the magnetic field. The results are shown in the time course of FIGS. 16A-16I (showing the magnetic field simulation in oil). In theory, the magnetic field is perpendicular to the electric field, and the direction of the magnetic field can be determined by the right hand rule according to the power flow direction. This is consistent with a typical transverse electromagnetic wave (TEM). Since the direction of the electric field is known, the magnetic field is expected to point outward. FIGS. 16A-16I verifies the direction of the magnetic field.

Figure 17:
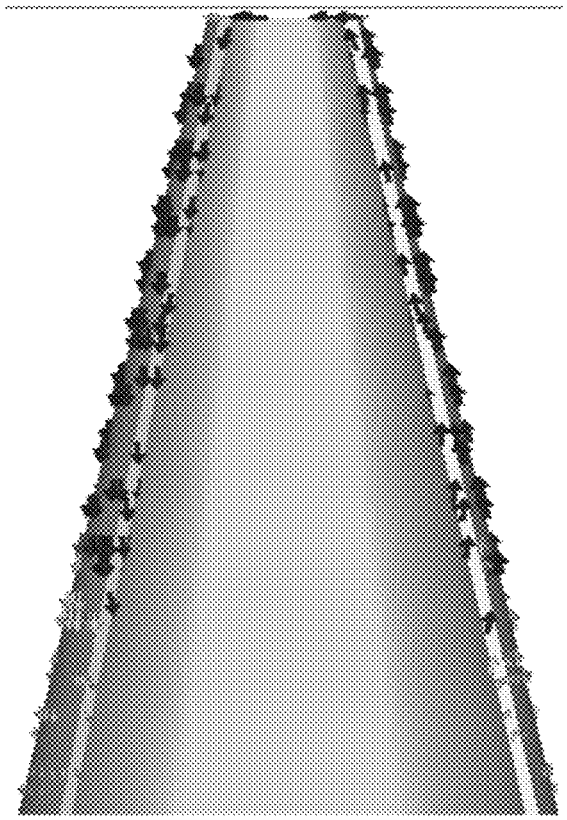
FIG. 17 illustrates a simulation of the current distribution of a "perfect electric conductor" (PEC) forming a triangular conductive plate (e.g., the antenna portion) of one variation of a resistively loaded dielectric biconical antenna.
Figure 18:
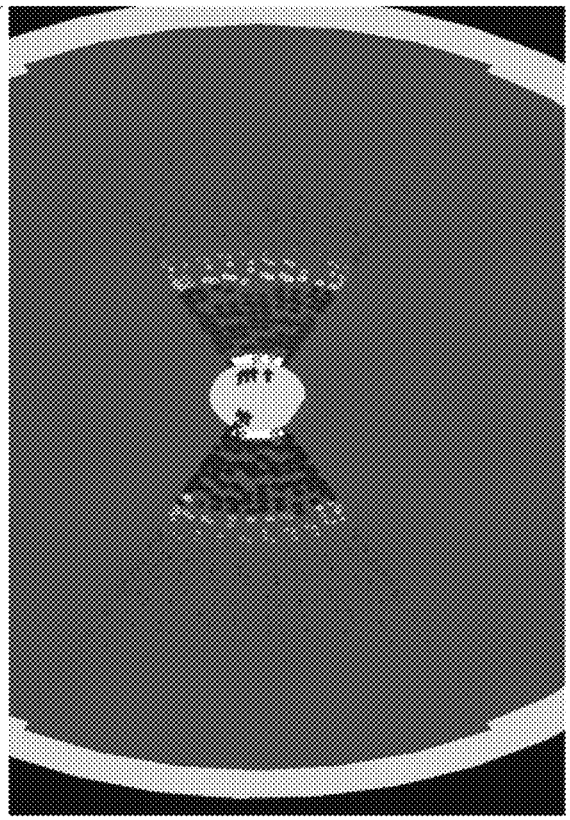
FIG. 18 illustrates the displacement current within the conductive plates of the simulation of FIG. 17.
Figure 19A:
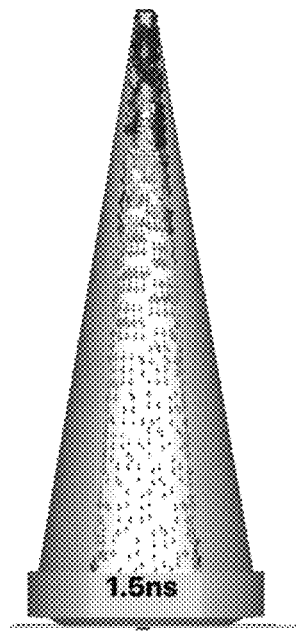
FIGS. 19A-19F illustrate examples of a simulation of current flow for a travelling wave in the conductive plates of a resistively loaded dielectric biconical antenna over time.
Figure 19B:
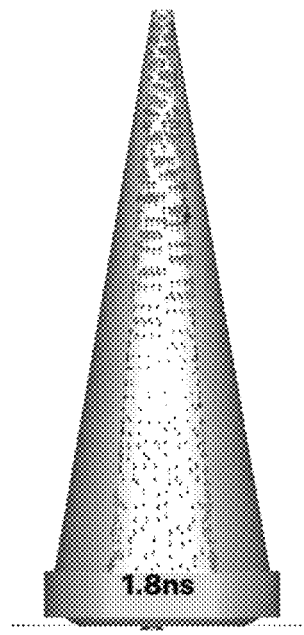
Figure 19C:
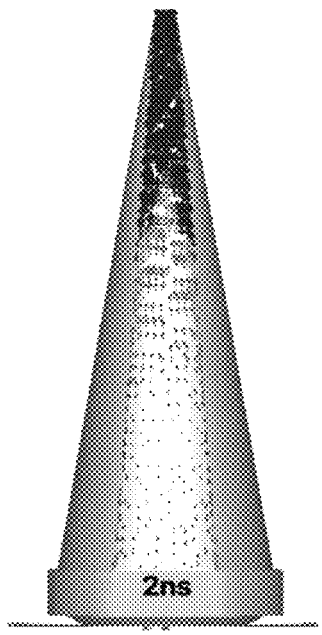
Figure 19D:
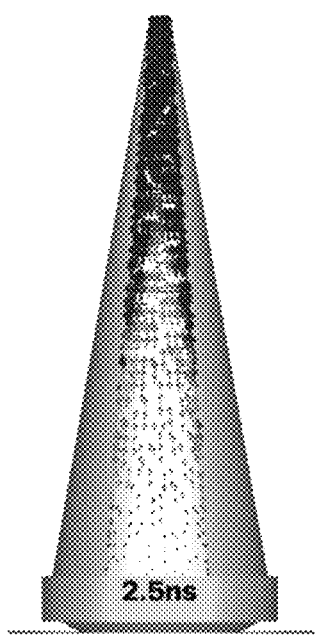
Figure 19E:
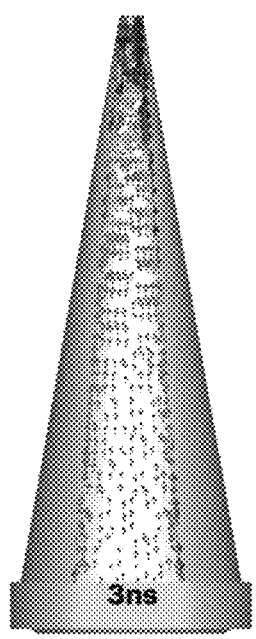
Figure 19F:
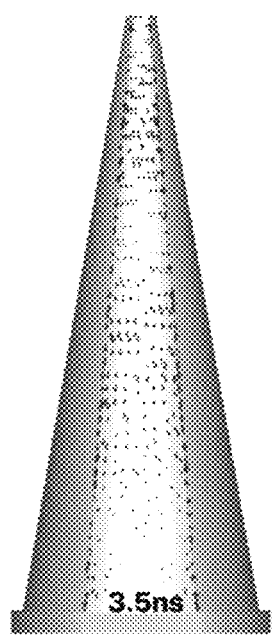

Next, a simulation was carried to determine the surface current distribution. The direction of the current is also can be determine using the right hand rule (Ampere's Law) by knowing the magnetic field direction. The current is expected to flow from left to right across the wave port signal (FIG. 17, showing current distribution of the PEC triangular PEC cone). Inside the antenna body (shown in FIG. 18), the current continues in the form of displacement current, which is governed by the electric field.

FIGS. 19A-19E show a current flow for a travelling wave at 1.5 ns (FIG. 19A), 2.5 ns (FIG. 19D), and 3 ns (FIG. 19E), for which the current direction throughout the V-shape plates is uniform although the intensity is not necessarily uniform. The current that has a standing wave feature is shown at 1.8 ns (FIG. 19B) and 2 ns (FIG. 19C), for which two current directions coexist on the plate. This observation suggests the impedance of the antenna is not matched completely and therefore causes some return to the source. The overlapping of the forward wave and backward wave causes zero current. But the location of the zero current is not at the antenna emitting section, which is beneficial for the antenna radiation. To reduce the reflection, the antenna can be loaded with a distributed resistance and the resistance profile can be prescribed. A single resistor ring at the end of the antenna may absorb the low frequency components and reduce the reflection. A simulation was carried to show the usefulness of the resistor ring. In this case, the input pulse has a fast rising phase and slow decay phase, which provides both low frequency and high frequency components. Note that low frequency components are beneficial to generate high amplitude pulse. But they are not radiated out to deep targets. It is however possible to guide them through a conductive path, i.e., having the resistor ring to contact the target through conduction medium. The resistor ring acts as a pair of electrodes, which are responsible for slow part of the pulse, whereas the wave emitting section radiates out fast part of the pulse.

Figure 20:
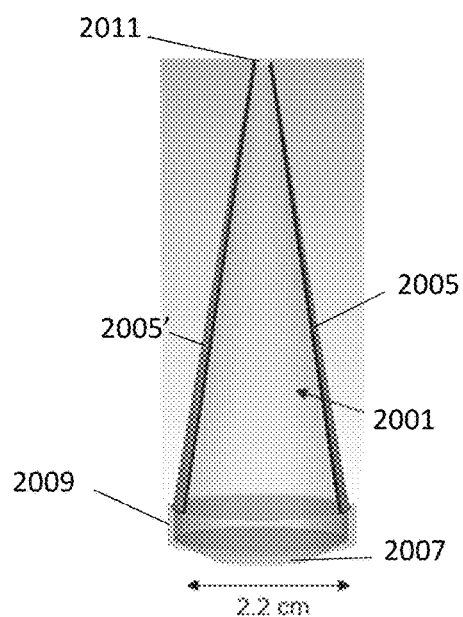
FIG. 20 is a schematic model of one variation of a resistively loaded dielectric biconical antenna.
Figure 21:
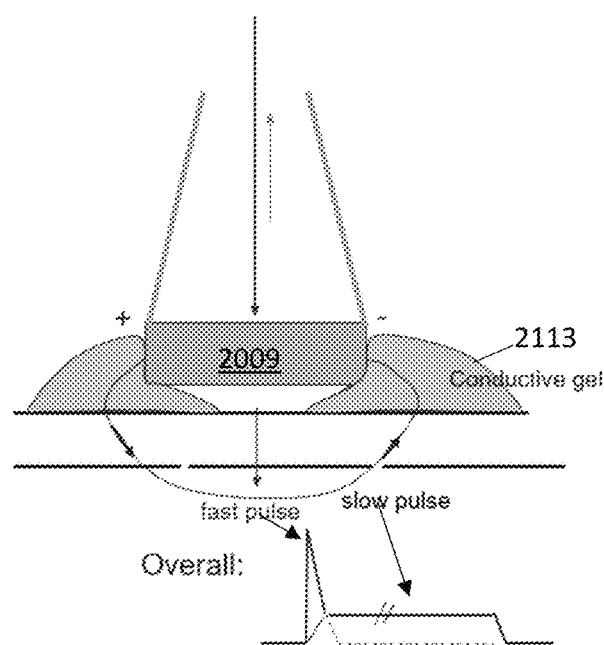
FIG. 21 illustrates the application of a resistively loaded dielectric biconical antenna such as the one shown in FIG. 20 applied to tissue, schematically illustrating paths for fast and slow pulses.
Figure 22A:
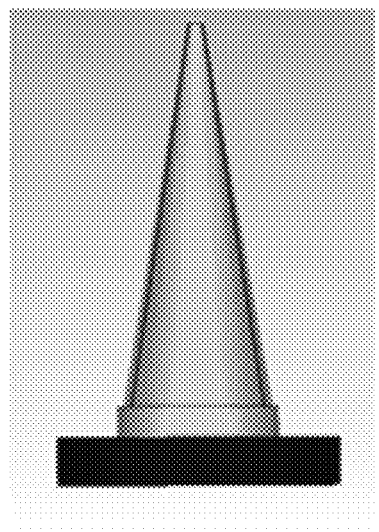
FIG. 22A schematically illustrates one example of a resistively loaded dielectric biconical antenna on a water surface (water may be used to simulate tissue to show penetration).
Figure 22B:
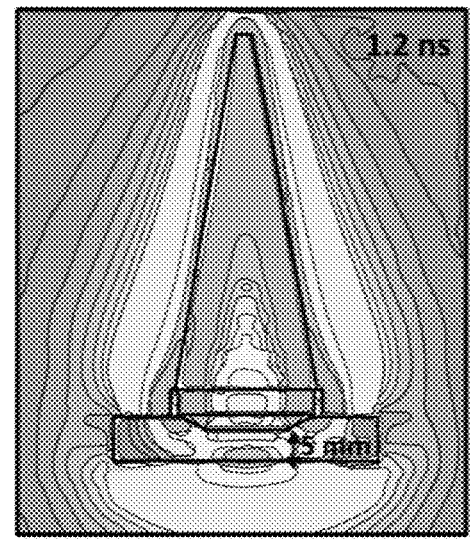
FIG. 22B is a heat-map showing the simulated relative intensity of the electric field showing penetration into the water model for this example of a resistively loaded dielectric biconical antenna.

FIG. 20 illustrates one example of an antenna 3D model, similar to that shown in FIGS. 1A-1C, and FIG. 21 shows the apparatus of FIG. 20 in contact with a tissue, showing the effect of fast and slow pulsing. The resistor ring 2009 may provide a resistance at the end of the apparatus (distal end of the apparatus) that reduces the electrical reflection within the apparatus and protects the pulsing apparatus. The resistor ring may also provide a current path for longer pulses to the tissue. As described above, the resistively loaded dielectric biconical antenna apparatus may include a dielectric cone 2001 on which one or more pairs of conductive (antenna) plates 2005 are attached. A resistor ring 2009 is positioned over a conical wave-emitting section 2007 at the distal end. The apparatus is fed from the proximal end 2011. As shown in FIG. 21 (upper) the resistor ring 2009 may contact the tissue through a conductive gel 2113. FIGS. 22A and 22B show the simulated profile in a water sample.

The results show that the antenna is able to deliver a pulse to a target at a depth of 5 mm at 1.2 ns (see, e.g., FIG. 22B). The field is largely confined to the center of the antenna (e.g., see FIGS. 23A-23D, showing the simulation of the produced electric field at specific time and its focal point).

In general, the use of a resistor ring (e.g., forming the resistively loaded dielectric biconical antenna) greatly increases the maximum electric field that penetrates into the tissue. For example, FIG. 24A shows a graph of electric field over time. In FIG. 24A, with the resistor ring attached between the conductive plates at the distal end (around the wave-emitting section), the electric field is much higher than that without the resistor ring. The pulse width is also longer. This waveform shows that the field consists of two parts: first, a radiated field, which is proportional to the time derivative of the input pulse (in this case, it is a ramp pulse) and second, the original pulse. The second pulse is only seen when the resistor makes contact with water. The first part is the result of the displacement which counts towards the radiation term and the second part is the result of current conduction through a resistive path. The behavior of the resistively loaded dielectric biconical antenna may therefore be modulated by the properties of the resistor ring. For example, FIG. 24B shows the e-field produced by various conductance values for the resistor ring.

EXAMPLES

A first example of a resistively loaded dielectric biconical antenna apparatus as described above, e.g., such as shown in FIGS. 25A-25C, 26 and 27, was used to treat a porcine tissue model (e.g., pig skin and fat). To characterize the antenna performance in real tissue, pig belly was used as target tissue for antenna exposure. The belly has several tissue layers, including skin, fat and muscle. In this example, illustrated in FIGS. 25A-25C, two holes were created in the fat layer at depths of 5 mm and 10 mm from the skin (shown in FIG. 25C) and electric field sensors 2505, 2505' were placed in the tissue using these holes. The electric field sensors 2505, 2505' used were connected to an optic fiber. The sensors may include, for example, a transverse probe 2505 that measures the field perpendicular to the fiber and a longitudinal probe 2505' that measures the field in line with the fiber. In the experiments, the belly was placed in a water bath (shown in FIG. 25A). For each hole, two probes were inserted in and the data were taken. The measurement results for a 1 kV input voltage and the simulation results are shown in FIG. 27, showing the produced electric field at specific time and its focal point for measured vs. simulated values (FIG. 26 is a schematic showing the placement of the antenna apparatus on the skin). They are comparable and appear in the same range. In general, the transverse probe measurement gives lower value than the simulated one, whereas the longitudinal probe gives higher. A graph of the results are shown in FIG. 27, showing that for 1 kV input, the electric field at 5 mm and 10 mm is 0.15 kV/cm and 0.09 kV/cm for the longitudinal probe, means that the field would be 7.5 kV/cm and 4.5 kV/cm respectively.

Figure 28:
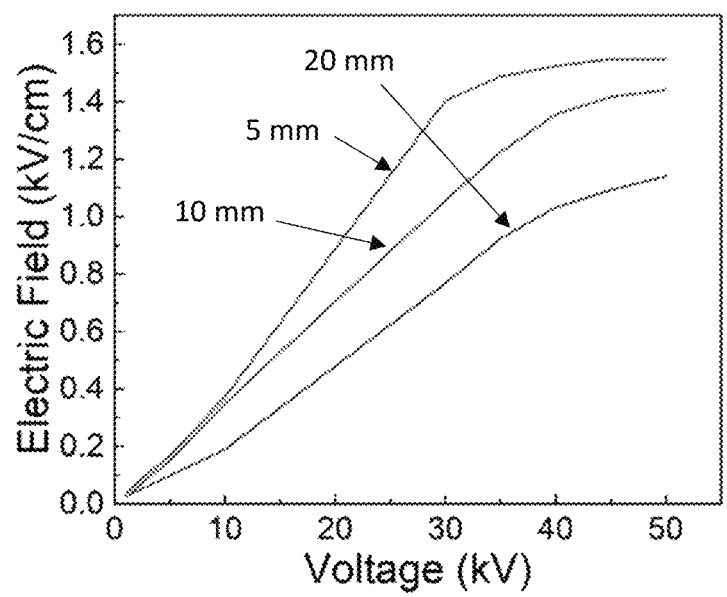
FIG. 28 is a graph showing the peak electric field at different depths depending on the peak voltage applied by the pulses.
Figure 29:
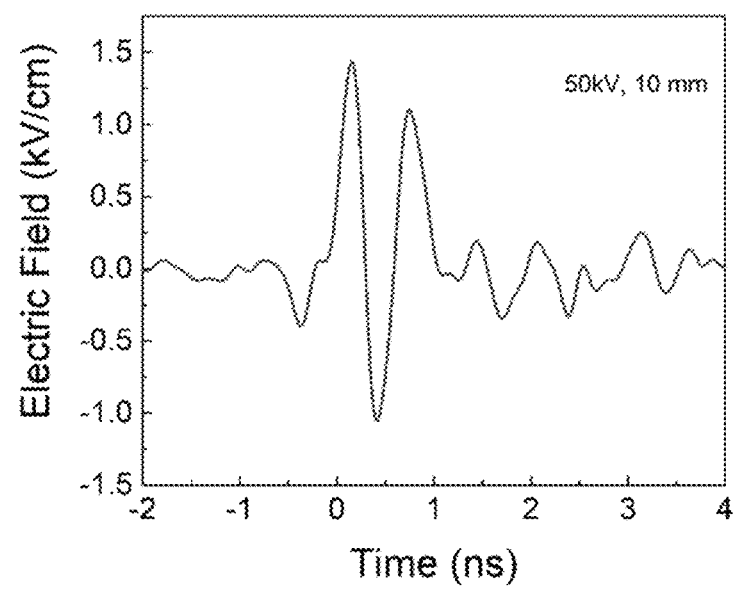
FIG. 29 shows an example of an electric field at its focal point for a single exemplary pulse (showing sub-nanosecond pulsing at 50 kV).

Electric field measurements were also performed in water at high voltages, by increasing the voltage gradually to 50 kV. To maintain the consistency with the pig tissue experiments, water was used as a tissue simulant. The results are shown in FIG. 28 and FIG. 29. At all three locations, the electric fields increase linearly as input voltage increases until 30-40 kV. The electric field did not substantially increase even the voltage increased. At 5 mm, the maximum electric field was obtained as about 1.5 kV/cm for 30 kV, whereas it was 1 kV/cm for 40 kV at 20 mm. FIG. 28 shows the produced electric field at specific times, and FIG. 29 shows the electric field at its focal point.

Figure 30:
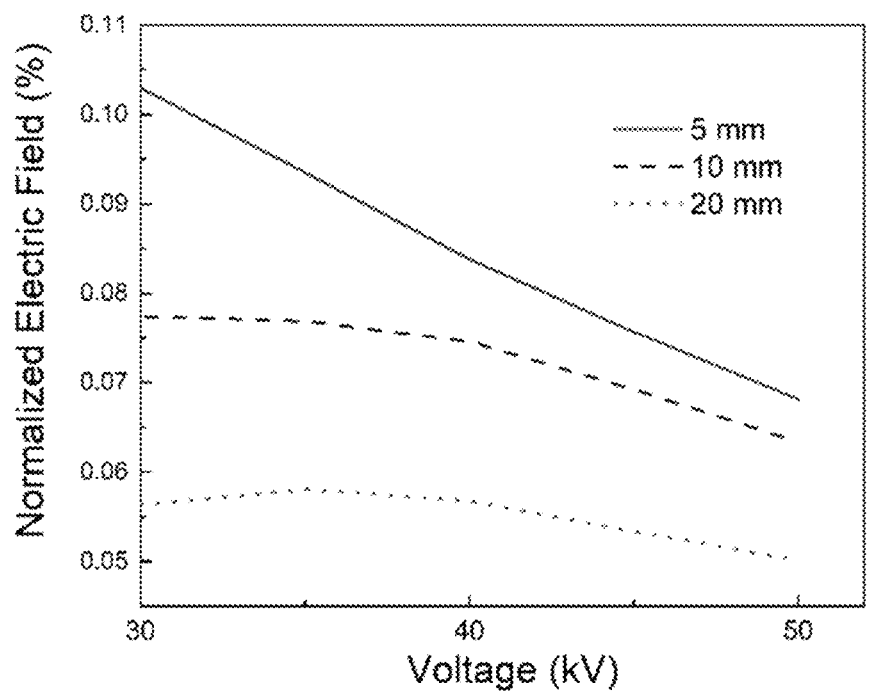
FIG. 30 is a graph showing the normalized electric fields at various applied voltages (between 30 kV to 50 kV) at different depths into the tissue.

To evaluate the performance of an exemplary antenna/applicator, the measured field was compared with the field created by a parallel electrode gap that has the same gap distance as the antenna aperture and is energized with the same applied voltage. For an input voltage of 30 kV and at 5 mm from the antenna tip, the field was measured to be ~10% of that created by a parallel gap. At 20 mm, the field dropped to ~5.6% (see, e.g., FIG. 30). These field levels were 2-3 fold less than the prediction from the CST simulation. This discrepancy could be due to the dielectric loss inherent to the dielectric material, which was not taken into account in the simulation. As the input voltage was increased to 50 kV, the field dropped to 6.8% and 5%, which shows that the radiation efficiency decreases as the input voltage increases. This decline of the efficiency may be caused by the nonlinearity of the dielectric material. When a dielectric material is applied with a high electric field, the dielectric polarization may exhibit a non-linear behavior, which may lower the actual dielectric constant and cause a higher dielectric loss. This nonlinear dielectric behavior was also observed in low c antenna, for which the radiated field did not increase linearly according to the input voltage. Thus, the apparatuses and methods described herein may use a dielectric material that is capable of holding high voltages and in the meantime maintaining the dielectric constant. In terms of the absolute electric field value, the maximum field was measured in these examples was 1-2 kV/cm within a distance between 5 mm and 2 mm from the antenna aperture. In this case, the antenna was fed 50 kV. For the low c antenna the maximum field may be higher.

Figure 31:
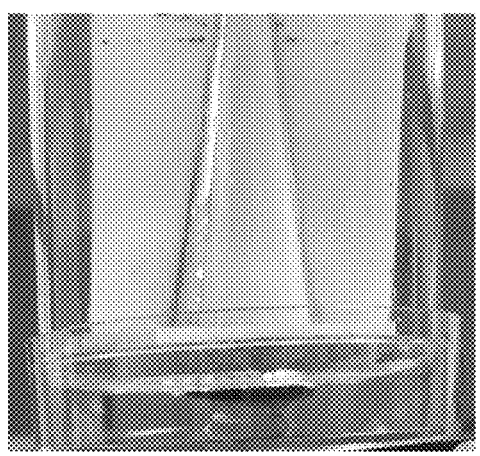
FIG. 31 shows one prototype resistively loaded dielectric biconical antenna applied to a liquid medium (e.g., water) in a dish.
Figure 32:
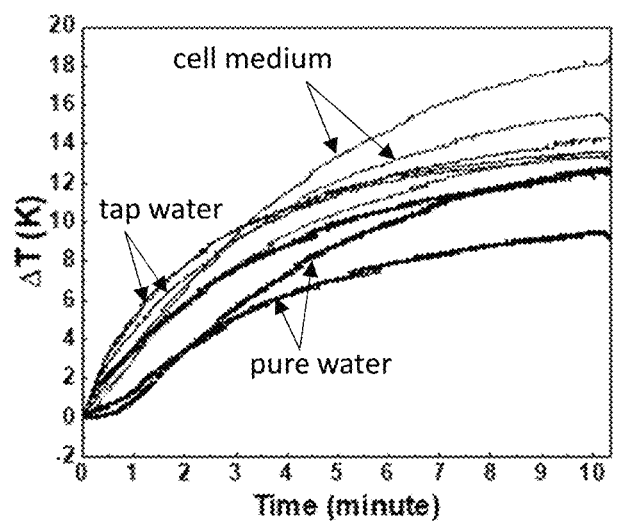
FIG. 32 is a graph showing the change in temperature in different liquid medium (e.g., tap water, cell medium, pure water) at different times.

Any of the apparatuses and methods described herein may also apply thermal effects. When electric pulses are repetitively applied to a medium or tissue, the temperature will increase. To show whether this antenna is capable of doing that, we pulsed 0.5 mL under the antenna (in a setup such as that shown in FIG. 31). Three samples were tested: cell medium, tap water, and pure water. An optic fiber sensor was used to measure the temperature change. At a source voltage of 30 kV, an electric field of 1-2 kV/cm can be produced in water as shown in the electric field measurement. We set pulse rate at 1 kHz and continued pulsing for 10 minutes While cell medium that has the highest conductivity exhibits the highest temperature increase and pure water the least, the temperature increase for these media are in the range of 12–18° C. from room temperature. FIG. 32 shows that the radiation efficiency decreases as the voltage increases. The conductivities of cell medium ($\sigma=1$ S/m), tap water (1 mS/m), and pure water (1 µS/m) differ by orders of magnitude, yet the temperature increases only differ by a few times, suggesting that dielectric heating is the main mechanism, not Ohmic heating.

Figure 33:
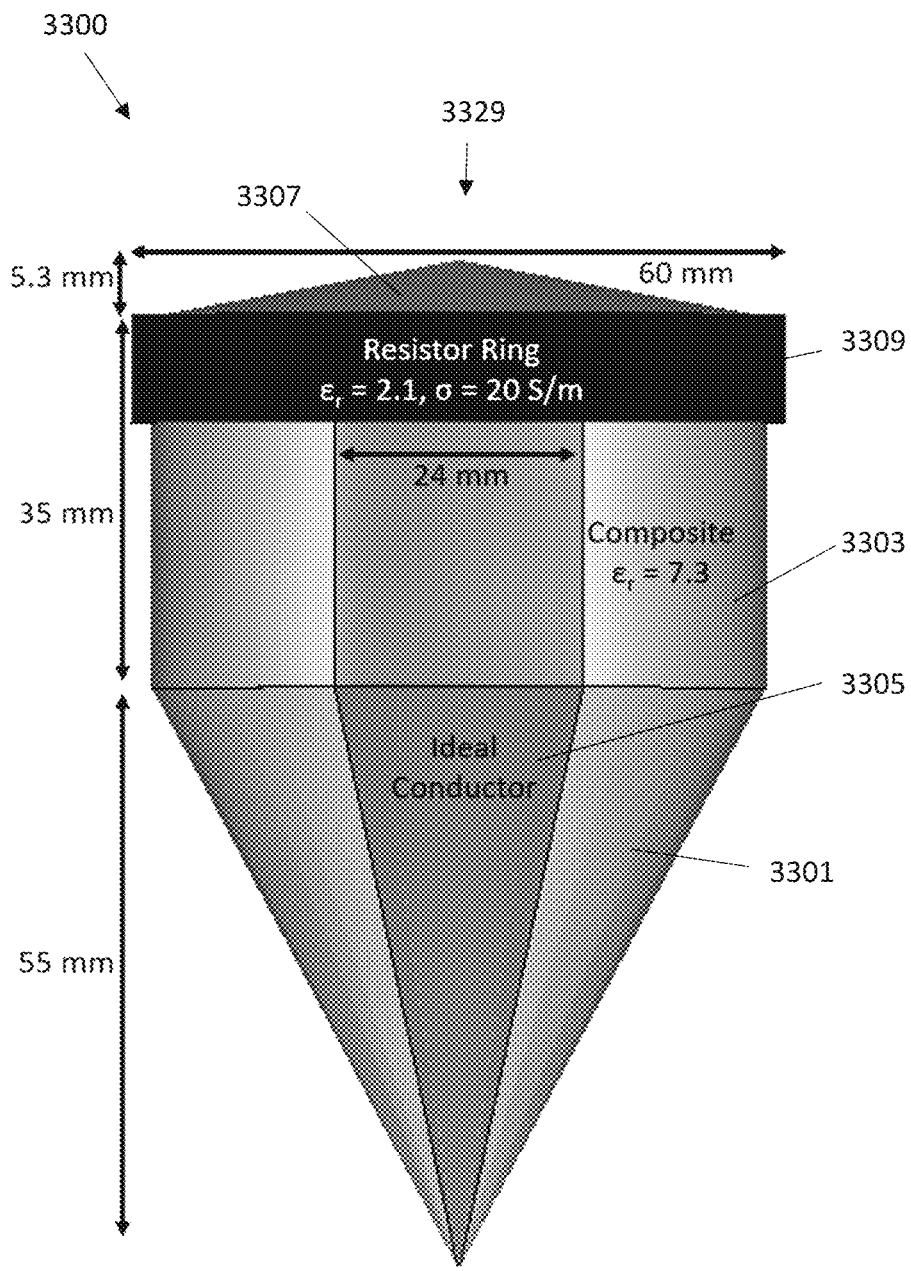
FIG. 33 is a schematic illustration of one example of a resistively loaded dielectric biconical antenna having a low epsilon value (e.g., a low dielectric constant).

Both low-permittivity (low $\varepsilon_r$, also referred to for convenience as low-dielectric) and high permittivity (high $\varepsilon_r$, also referred to for convenience as high-dielectric) antennas are described herein, and may be configured as described above. For example, FIG. 33 illustrates one example of a low-dielectric antenna/applicator 3300 that has a material of dielectric constant of 7.3. It has a conical wave launcher or cone region 3301 and emitter 3307. A dielectric rod 3303 is inserted between for wave guidance. The conductive plates 3305 extend down the proximal-to-distal length of the conical wave launcher and the cylindrical (dielectric rod) portions. The conductive plates connect to the resistor ring 3309 around the emitter. The dielectric rod antenna may be constructed from a nanocomposite material having an $\varepsilon_r$ of about 7.3. The launching section may be constructed using copper tape, e.g., and may have an impedance of about 50Ω according.

Figure 34:
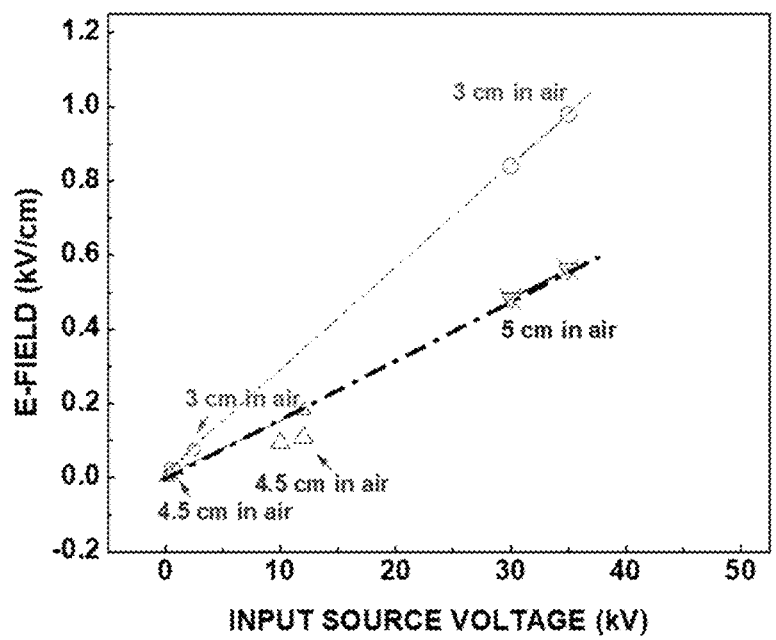
FIG. 34 is a graph showing the input source voltage vs. electric field in air at different distances from the resistively loaded dielectric biconical antenna distal end (e.g., the emitting end).
Figure 35:
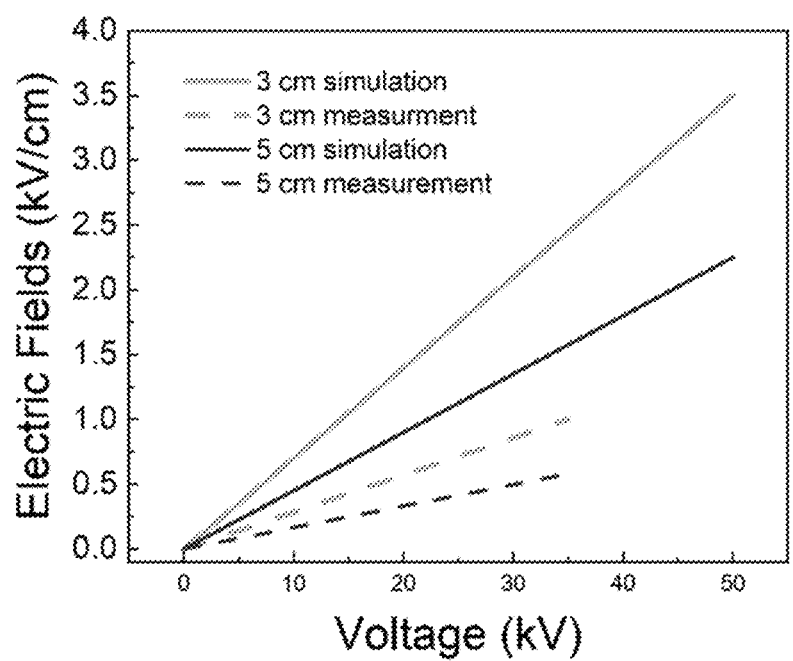
FIG. 35 is a graph showing the input source voltage vs. electric field for a resistively loaded dielectric biconical antenna, comparing measured (in water) vs. simulated fields at different distances from the emitting end of the resistively loaded dielectric biconical antenna.

FIGS. 34 and 35 illustrate both simulation and measured values for electric fields at various depths from the resistively loaded dielectric biconical antenna using short pulses of electrical energy. In FIG. 34, the e-field at various distances in air are shown (for both 3 cm and 5 cm) at various input source voltages. FIG. 35 is a graph showing the electric field for simulated and measured values at various depths (e.g., 3 cm, 5 cm).

Figure 36A:
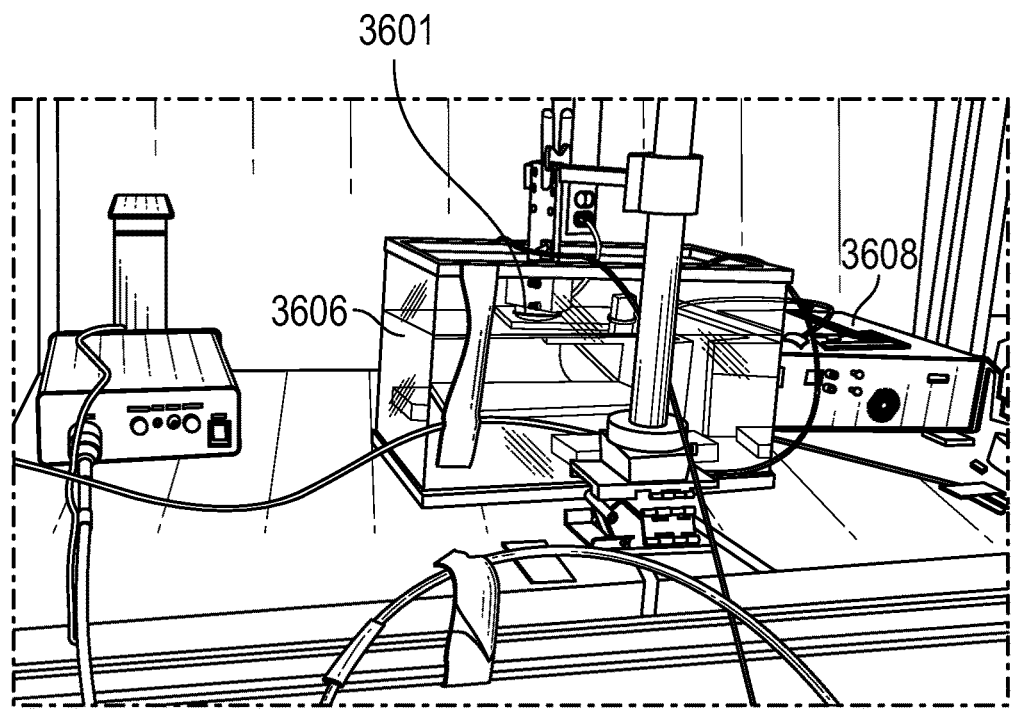
FIGS. 36A-36B illustrate one example of an experimental setup for testing a resistively loaded dielectric biconical antenna system in water.
Figure 36B:
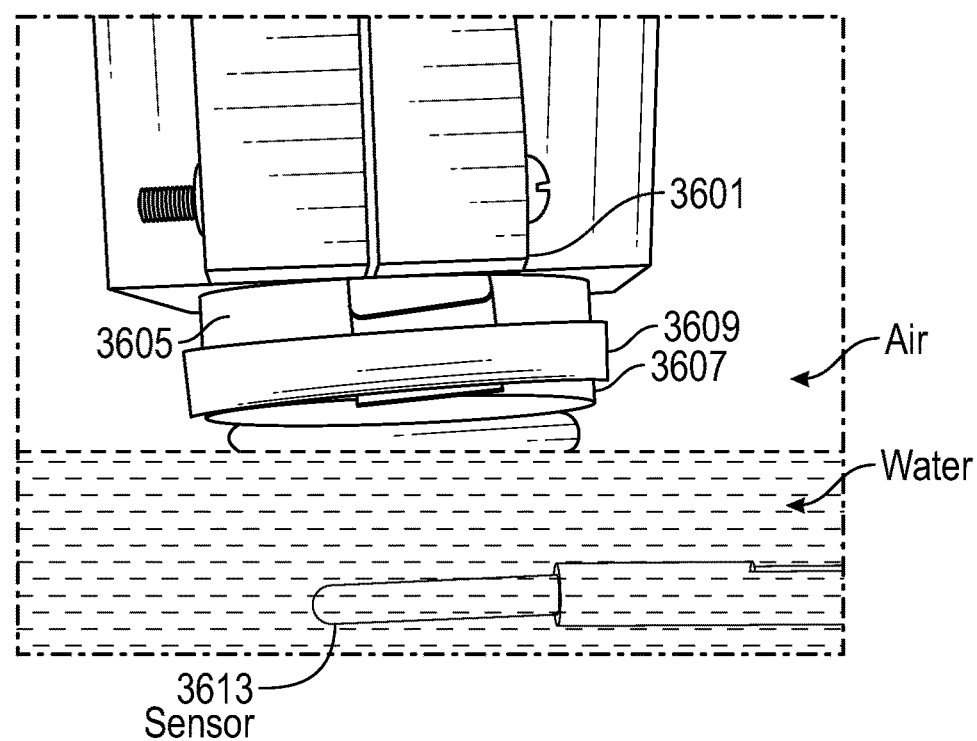
Figure 37:
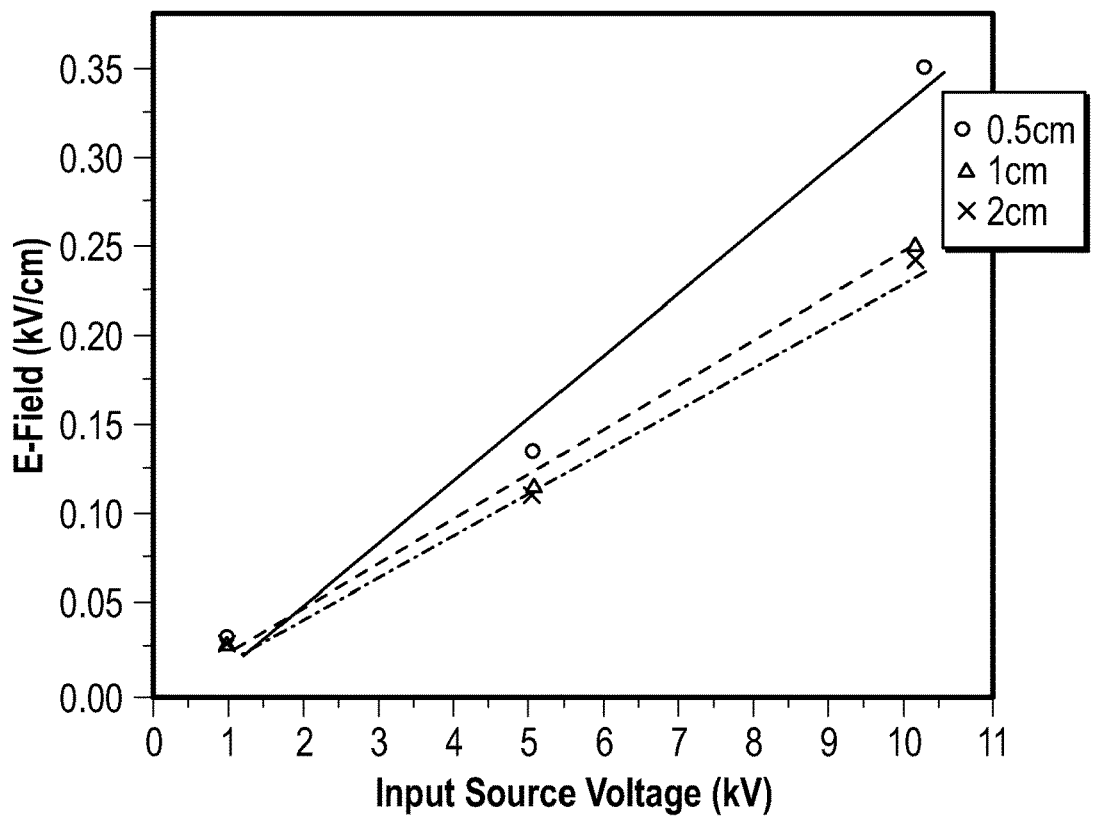
FIG. 37 is a graph showing the electric field vs. input source voltage for the resistively loaded dielectric biconical antenna example system shown in FIGS. 36A-36B at low voltages.
Figure 38:
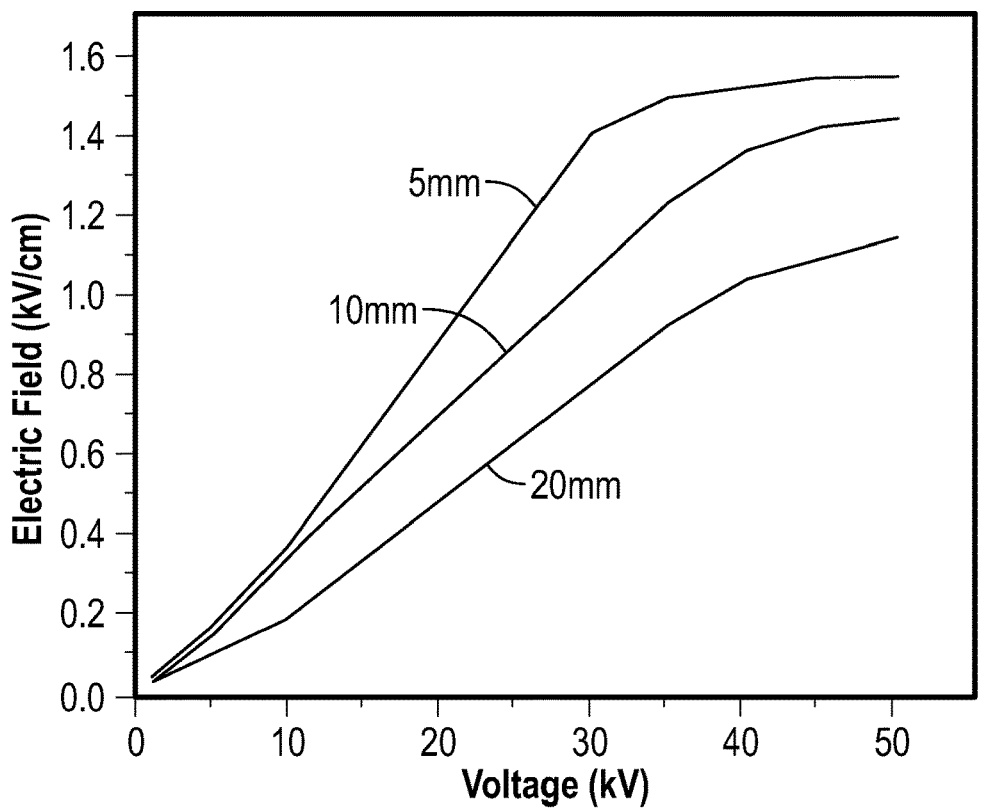
FIG. 38 is a graph showing the electric field vs. input source voltage for the resistively loaded dielectric biconical antenna example system of FIGS. 36A-36 over a broader voltage range.

Experiments on a prototype low dielectric (low $\varepsilon_r$) antenna/applicator similar to that shown in FIG. 33 were performed to examine the depth of penetration of the electromagnetic field. FIGS. 36A and 36B shows an experimental set-up for testing a low dielectric antenna/applicator 3601 in a tank of water 3606. A high-voltage pulse generator 3608 is connected to the resistively loaded dielectric biconical antenna 3601, which may be configured as shown and described above, and includes the resistor ring 3609 around the conical wave-emitting distal end 3607 and in electrical contact with the conductive plates 3605 extending on opposite sides of the proximal dielectric cone (not visible in FIGS. 36A-36B). A sensor 3613 is placed beneath the resistively loaded dielectric biconical antenna at a fixed distance in order to determine the delivered electric field within the water. FIG. 37 and FIG. 38 (note that FIG. 38 is identical to FIG. 28, discussed above) illustrate the results for different ranges of input voltages. As shown in FIG. 37, the electrical filed increases linearly as the input source voltage (kV) increases at various distances (2 cm, 1 cm, 0.6 cm). At larger voltages the electric field at depth plateaus, for this particular tested dielectric material, at above about 30 kV, though the electric field at the target is greater than about 1 kV/cm, even at a depth of about 2 cm.

Thus, both high epsilon (e.g., high dielectric) and low epsilon material apparatuses as described herein that are resistively loaded (e.g., with a resistor ring around all or part of non-emitting surface of the distal conical wave-emitting section) may have advantages. For example, low-epsilon antenna/applicators may be more efficient at lower voltages (e.g., voltages below about 10 kV) as compared to similar higher-epsilon apparatuses, and may have larger apertures (e.g., ~6 cm, 10 kV, average field: 1.67 kV/cm in the aperture), whereas higher-epsilon apparatuses may have a smaller antenna aperture size (e.g., ~2.2 cm, 10 kV, average field: 4.5 kV/cm in the aperture). Both high-epsilon and low-epsilon apparatuses may generate approximately the same field at 0.5 mm, 0.35 kV/cm in at least some of the examples described herein. Typically at least 1-1.5 kV/cm may be generated within 2 cm depth for a feed voltage of 50 kV. Other dielectric materials may have greater field strength with larger voltages (e.g., greater than about 30 kV).

Figure 39:
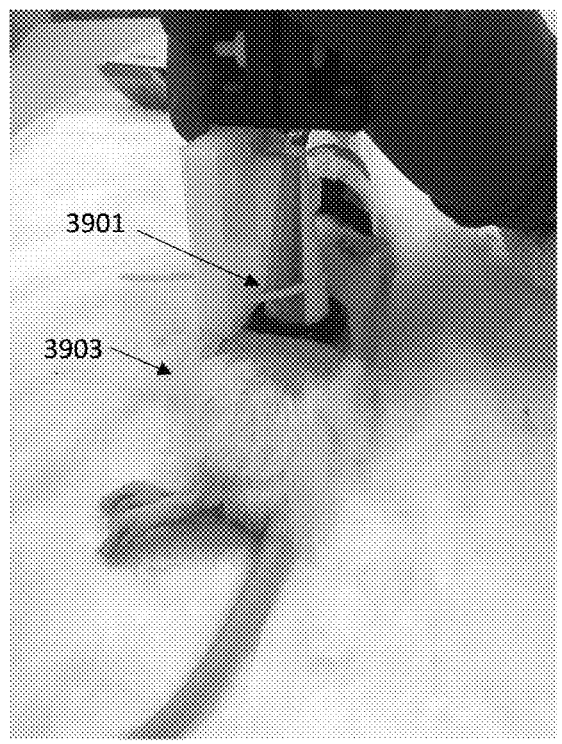
FIG. 39 illustrates the use of a prototype resistively loaded dielectric biconical antenna applicator to non-invasively treat sub-dermal fat cells in a rat.
Figure 40:
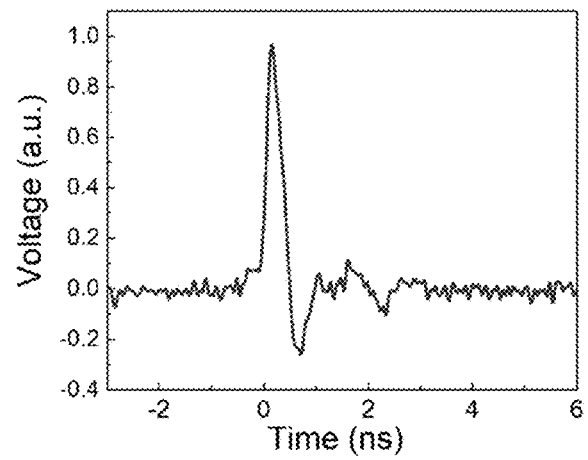
FIG. 40 is a graph showing an example of a sub-nanosecond pulse applied to the skin of a rat.

The methods an apparatuses as described herein were used to treat tissue in an animal model (e.g., an obese rat model). For example, FIG. 39 illustrates the use of a prototype antenna applicator 3901 non-invasively on the skin of a rat 3903 in order to target sub-dermal fat cells (adipose), to induce apoptosis of adipose tissue. In this example, multiple treatment region on the skin were treated with the apparatus and nanosecond pulses of voltage applied (see, e.g., FIG. 40).

The antenna apparatuses, such as resistively loaded dielectric biconical antenna apparatuses, described herein may be configured for use with very short pulses (nanosecond, sub-nanosecond, e.g., picosecond pulses). For example, an antenna apparatus configured as a resistively loaded biconical antenna apparatus may include a first (proximal) dielectric cone section having a low- or high-dielectric constant material (e.g., in some variations the dielectric constant is between 3-20 for low dielectric materials, and greater than 20 for high dielectric material, such as materials having a dielectric constant of about 28) and a resistor ring encircling the sides of a second (e.g., distal) conical section that include a distal-facing wave-emitting face. In some variations, the antenna radiated field intensity may be increased by the use of a low dielectric constant material for the antenna (e.g., less than 15, less than 12, less than 10, etc.). For example, a material such as a polyvinylidene fluoride (e.g., Kynar) may be used, which has a dielectric constant of 8.5 and high dielectric strength (e.g., of about 1700 V/mil). In general, the dielectric materials forming the apparatus may be high dielectric strength materials (e.g., having a dielectric strength of greater than about 1200 V/mil, 1250 V/mil, 1300 V/mil, 1350 V/mil, 1400 V/mil, 1450 V/mil, 1500 V/mil, 1550 V/mil, 1600 V/mil, 1650 V/mil, etc.). The dielectric may be a plastic material that is easy to machine.

In any of the apparatuses described herein, the antenna may be low impedance, i.e., the area of the conical, V-shape metal plates may cover the cylindrical dielectric waveguide (e.g., dielectric rod) as much as possible, without causing too much of an impedance mismatch between source and the antenna.

In any of the apparatuses and methods described herein, the pulse waveform may be multiphasic and/or monophasic. In the examples described above, the pulses (e.g., sub-microsecond pulses) are multiphasic, but can instead be monophasic, e.g., by reducing the diffraction at the end of the V-shape metal plates. For example, a round-edged plate rather than a sharp-edged plate can be used.

Any of these apparatuses may be fed by, e.g., a parallel-plate transmission line that is connected, e.g., through a coaxial cable, to a pulse generator, such as a picosecond pulse generator. The pulse generator typically delivers a high voltage (e.g., between about 1 kV to about 100 kV or more, such as between about 1 kV to about 50 kV, between about 10 kV to about 50 kV, etc.), but very short (e.g., nanosecond, sub-nanosecond, etc.) pulses. A portion of the resistively loaded dielectric biconical antenna may be housed in an oil container to help withstand the large voltage and avoid air breakdown. As described above, these apparatuses typically include a resistor ring (e.g., at the end of the dielectric antenna) to reduce the reflection and protect the puling source. Although the term 'ring' is used in all of the examples described herein, it should be understood that the shape need not be circular, as long as it circumscribes the wave-emitting section, e.g. the lateral sides of the wave-emitting section (in some variations, avoiding the wave-emitting distal-facing face of the wave-emitting section) that is exposed to air that allows it to interface with water or tissue. The distal facing surface of the wave emitting section of any of the antennas described herein may be referred to as the face of the antenna. Returning now to FIG. 33, for example, the distal face 3329 is shown as a tapering, conical shape, generally facing the distal end of the apparatus. Thus the distal face of the apparatus does not need to be flat and may be conical.

In some variations, the resistively loaded dielectric biconical antenna apparatuses described herein may deliver electric fields of greater than 1-2 kV/cm in the tissue, at depths of greater than 0.5 cm, greater than 1 cm, greater than 2 cm, etc. For example, the distal end of the resistively loaded dielectric biconical antenna (e.g., the distal face of the wave emitting section) was submersed in water and the rest of the antenna was kept above the water, and an optic probe (Kapteos, France) was used to measure the electric field in water. The relationship between input voltage and radiated field is linear for the voltages below 30 kV, as described above in FIGS. 37-38. In on example, the maximum field is 1.5 kV/cm for a depth of 5 mm and the minimum field is 1.0 kV/cm for a depth of 20 mm.

Any of the methods of using the antennas described herein may be used to induce changes in the tissue being treated. Changes may include but are not limited to: cell death (e.g., apoptosis), stimulation (e.g., electrical stimulation), evoking an inflammatory response (e.g., releasing one or more cytokines, etc.), increasing cell function (e.g., increasing release and/or uptake), suppressing cell function (e.g., suppression of release or uptake), changes in metabolic activity, or any combination of these. These changes in the cells may lead to changes in the tissue and are caused noninvasively by cells receiving the applied treatment from the resistively loaded dielectric biconical antenna. For example, as described above in a rat mode in FIG. 39, high-voltage pulsed energy (e.g., between 20-50 kV/cm) applied in at sub-microsecond (e.g., sub-nanosecond, and/or picosecond) pulsing resulted in cell death to a depth of greater than 2 cm. In any of the apparatuses and methods described herein, cells may be treated at a sub-apoptosis threshold. Specifically, the electric field in the tissue (e.g., at between about 0.1 and 5 cm, at greater than 0.5 cm, greater than 1 cm, greater than 1.5 cm, greater than 2 cm, etc.) may be between 0.5 kV/cm and 20 kV/cm (e.g., between 0.6 kV/cm and 10 kV/cm, between about 0.7 kV/cm and about 5 kV/cm, including any of greater than about 0.5 kV/cm, greater than 0.6 kV/cm, greater than 0.7 kV/cm, greater than 0.8 kV/cm, greater than about 0.9 kV/cm, greater than 1 kV/cm, etc. and less than about 1.2 kV/cm, less than about 1.5 kV/cm, less than about 2 kV/cm, less than about 2.5 kV/cm, less than about 3 kV/cm, less than about 5 kV/cm, less than about 10 kV/cm, less than about 15 kV/cm, less than about 20 kV/cm, less than about 30 kV/cm, etc.), and may modify cellular function (e.g., stimulating or suppressing cell functions). For example, the resistively loaded dielectric biconical antennas described herein may be used to apply energy of greater than 0.5 kV/cm to induce a local (and/or general) cell immune response in the tissue at depths of greater than 1 cm, greater than 1.5 cm, greater than 2 cm, etc. Sub-nanosecond pulsing (e.g., picosecond pulsing) using the resistively loaded dielectric biconical antenna apparatuses described herein may be used to treat any cell type, including, but not limited to adipose (e.g., fat), skin (dermal) cells, neural cells, dendritic cells and/or macrophages. The wide safety margin makes the resistively loaded dielectric biconical antennas described herein generally safe tools to be used in various applications.

For example, metabolic activity of dendritic cells can be promoted or suppressed by the application of sub-nanosecond pulsing using the antenna apparatuses described herein approximately 1 kV/cm (e.g., between about 0.7 kV/cm and 1.3 kV/cm). For macrophages, in some treatments virtually metabolic activity was suppressed. Pulse parameters (electric field, repetition rate, exposure time) may be varied in a wide range to modulate the effects. Metabolic activity for these cells may be reflected in changes in oxygen consumption, effects on the electron transport chain in mitochondria and mitochondrial production of reactive oxygen species. The apparatuses described herein may also be used to change metabolic and activity functions including macrophage phagocytosis.

Figure 41:
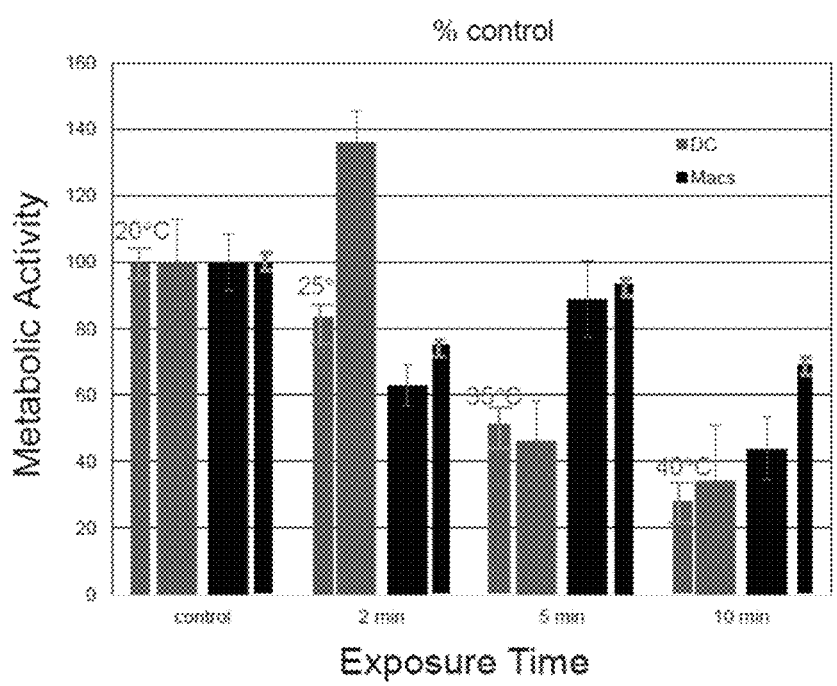
FIG. 41 illustrates the effects of the application of energy using an antenna as described herein to deliver picosecond pulsing to sets of dendritic cells and macrophage cells.

FIG. 41 illustrates an example of the suppression of dendritic cell activity, and also of macrophage activity, at different exposure times using an antenna as described above. In this example, immune dendritic cells (DC) and/or macrophage cells (Macs) were treated. In FIG. 41, the thick bars illustrate the antenna results. All treatments were done using an antenna setup similar to that shown in FIG. 31. For each condition, three replicates were used. The assays were done 24 hours after treatment by antenna pulses (e.g., 1 kV/cm, 1 kHz). The thin bars are the results for separate temperature control using a water bath whose temperature is controlled by a heater. Cells were contained in a test tube and were treated for a given time when the test tubes were immersed in water.

As shown for dendritic cells (DC), the application of energy as described herein can either promote metabolic activity (2-minute treatment) or suppress it (5 or 10-minute treatment) compared to the control. For macrophages (Macs), metabolic activity was general lower than the control after antenna pulse treatment. For the same conditions, the responses of dendritic cells and macrophages to antenna pulses are different (see, e.g., at 2 and 5 minutes). In general, dendritic cells are more susceptible to antenna pulses than macrophages. Further, it appears that the temperature increase caused by antenna pulses may play a role in causing these effects, as these effects can be "repeated" in water bath experiment, where the temperature was controlled precisely.

The apparatuses and methods described herein may also or alternatively be used to modulate expression levels of dendritic cell surface markers; for example, sub-nanosecond pulsing using a resistively loaded dielectric biconical antenna as described herein can downregulate expression levels of numerous dendritic cell markers, and in some cases result in transient early upregulation of cell marker expression for short exposure (<2 minutes). Thus, cell metabolic activity (e.g., in dendritic cells) may be remotely modulated by the non-invasive methods described herein, which may include applying energy to the surface of the tissue containing the target cells by employing the resistively loaded dielectric biconical antenna to penetrate, e.g., at least 0.5 cm into the tissue.

Methods of Treatment

A generic treatment method including any of the resistively loaded dielectric biconical antennas described herein may include, as a preliminary step, connecting or facilitating a connection of the antenna applicator (e.g., such as a resistively loaded dielectric biconical antenna as described above) to a source of pulsed voltage, and particularly a source capable of delivering high-voltage, nanosecond and/or sub-nanosecond, e.g., picosecond, pulses. In some embodiments the method may start when the antenna is already coupled to the pulse generator. Any of these methods may include placing the resistively loaded dielectric biconical antenna apparatus, such as the distal end face of the antenna applicator apparatus, against the tissue to be treated. The resistively loaded antenna is typically a resistively loaded biconical antenna apparatus that includes a proximal dielectric cone that is at least partially clad by one or more pairs of (e.g., triangular) conductive plates bent around the dielectric cone, the proximal dielectric cone includes a cylindrical region at the base of the dielectric cone and a distal region that tapers toward the distal end of the apparatus; a resistor ring structure is positioned around at least a portion of the distal region. The pulse generator may be connected to the proximal end (e.g., tip) of the proximal dielectric cone, and may be connected via a parallel plate feed, e.g., to a coaxial cable coupled to the pulse generator. Pulses may then be applied to the tissue through the resistively loaded dielectric biconical antenna, such as applying high voltage (e.g., between 5 kV/cm and 100 kV/cm, e.g. between 5 kV/cm and 70 kV/cm, between 5 kV/cm and 50 kV/cm, etc.), very fast, such as nanosecond and/or sub-nanosecond (e.g., picosecond) pulses to the tissue at a desired frequency (e.g., between 1 Hz and 1 MHz, e.g., between 500 Hz and 10 kHz, between 500 Hz and 5 kHz, between 500 Hz and 2 kHz, etc.) and for a desired treatment duration, e.g., between 1 second and 60 minutes, between 10 seconds and 45 minutes, between 10 seconds and 30 minutes, etc.). The resistively loaded dielectric biconical antenna may be applied with the distal end directly against the tissue (e.g., skin) and may delver energy having a peak electric field of between about 0.5 kV/cm and 50 kV/cm (e.g., between 0.8 kV/cm and 30 kV/cm, greater than 0.5 kV/cm, greater than 0.6 kV/cm, greater than 0.7 kV/cm, greater than 0.8 kV/cm, greater than 0.9 kV/cm, greater than 1.0 kV/cm, greater than 1.5 kV/cm, greater than 2 kV/cm, greater than 2.5 kV/cm, etc.), into the tissue to a depth of between about 0.1 and 3 cm (e.g., more than 0.5 cm, more than 1 cm, more than 2 cm, between 0.5 and 2 cm, etc.). The resistively loaded dielectric biconical antenna may be at least partially enclosed in an oil or other material to reduce or eliminate air breakdown of the resistively loaded dielectric biconical antenna. A conductive gel or other interface material may be used between the resistively loaded dielectric biconical antenna and the tissue.

The resistively loaded dielectric biconical antenna apparatuses and methods of using them described herein may be used in virtually any indication in which electrical stimulation may be applied. In general, any of the high frequency nanosecond pulse generators and methods of using them described herein may be used for a medical therapy.

For example, the methods and apparatuses of the present disclosure may be used for cardiac pacing, defibrillation, muscle training and rehabilitation, pain control, alleviation of disease symptoms, psychiatric disorders, and cancer ablation. They may also be used in neuromuscular and psychiatric disease diagnostics and research.

For example, the devices, systems and methods described herein may be utilized in various ablation procedures (e.g., radiation-based), dermatological procedures (e.g., treating various dermatological conditions, such as skin cancers), general surgery procedures (e.g., pancreatectomy), cardiology (e.g., valve repair), gynecology (e.g., hysterectomy), neurosurgery (e.g., tumor resection) etc.

Any of the methods described herein may be applied to excitable tissues (including but not limited to neuronal tissues) for either excitation and/or ablation or other tissue treatments. For example, described herein are methods and apparatuses for the stimulation of excitable tissues such as nerve and heart muscle, the treatment of neurological disorders such as epilepsy, Parkinson's disease and stroke. Heart disorders could include atrial fibrillation and ventricle fibrillation. As demonstrated above, the membrane potential of one or a group of cells may be excited directly using the methods described herein. The methods and apparatuses described herein may be used to stimulate secretion in cells such as platelets.

Any of the tissues described herein may be modified and/or their activity modulated using the resistively loaded dielectric biconical antennas described herein to apply nanosecond and/or sub-nanosecond (e.g., picosecond) pulses.

The resistively loaded dielectric biconical antenna apparatuses described herein may be used to non-invasively treat a patient's skin and/or the tissue immediately below the skin, including treatment of one or more of: acne, seborrheic keratosis, keloids, molluscum contagiosum, acrocordon, psoriasis, papilloma, human papilloma virus (HPV), melanoma, melasma, sebaceous hyperplasia, congenital nevi, syringoma, congenital capillary malformation (port-wine stains), melasma, actinic keratosis, dermatosis papulosa nigra, angiofibroma, skin tumors, aging skin, wrinkled skin, cherry angioma, epidermal/sebaceous cyst, basal cell carcinoma, aging skin, benign tumors, precancerous tumors, cancers and warts. These methods and apparatuses may also be used for cosmetic skin treatments, including tattoo removal, hair follicle destruction, scar/keloids reduction, fat reduction, and wrinkle reduction. For example, the methods and apparatuses described herein may be useful for treating melanomas by causing them to self-destruct. In general, these methods may be useful for in vitro treatment of skin lesions.

The methods and apparatuses described herein may be useful for nanoelectroablation and vaccination.

Thus, the methods and apparatuses described herein may be used in treatment of various diseases. A "disease"

includes any abnormal condition in or on a subject that is associated with abnormal, uncontrolled growths of tissue, including those that are cancerous, precancerous, and benign, or other diseases as known in the art. The methods and apparatuses of the present disclosure can be used for the treatment of any type of cancer, whether characterized as malignant, benign, soft tissue, or solid, and cancers of all stages and grades including pre- and post-metastatic cancers. Examples of different types of cancer include, but are not limited to, digestive and gastrointestinal cancers such as gastric cancer (e.g., stomach cancer), colorectal cancer, gastrointestinal stromal tumors, gastrointestinal carcinoid tumors, colon cancer, rectal cancer, anal cancer, bile duct cancer, small intestine cancer, and esophageal cancer; breast cancer; lung cancer; gallbladder cancer; liver cancer; pancreatic cancer; appendix cancer; prostate cancer, ovarian cancer; renal cancer (e.g., renal cell carcinoma); cancer of the central nervous system; skin cancer (e.g., melanoma); lymphomas; gliomas; choriocarcinomas; head and neck cancers; osteogenic sarcomas; and blood cancers.

These methods and apparatuses may also or alternatively be useful for ablating cancer and generating resistance to new cancer growth, including treatment of tumors. Examples of tumors include a benign prostatic hyperplasia (BPH), uterine fibroid, pancreatic carcinoma, liver carcinoma, kidney carcinoma, colon carcinoma, pre-basal cell carcinoma, and tissue associated with Barrett's esophagus.

The noninvasive delivery of nanosecond and/or sub-nanosecond (e.g., picosecond) pulse trains described herein may be effective in treating diseases including cancers because they may penetrate into the intracellular region of the cell(s). The ability to penetrate beyond the plasma membrane may be faster than the time required for intracellular and intraorganellar charges to redistribute to cancel the imposed field. This may allow the methods and apparatuses described herein to permeabilize small organelles by applying electrical pulses in the nanosecond range (e.g., including vesicles, mitochondria, endoplasmic reticulum and nuclei).

The methods and apparatuses described herein may also be useful for platelet activation (in the absence of thrombin); for example, these methods may be used for applying electrical pulses in the nanosecond range of platelet-rich plasma to improve wound healing and enhance blood flow.

As mentioned, above, the megahertz compression of nanosecond pulse bursts described herein may be used to influence tumor growth; for example, to treat tumors with electrical pulses in the nanosecond and/or sub-nanosecond (e.g., picosecond) range, so that the tumor disappears over days to weeks, and may exhibit characteristics of immunogenic cell death (ICD), e.g., releasing DAMPs such as calreticulin translocation from the ER to the cell surface, ATP release and HMGB1 release. These methods may also be used to inhibit metastasis.

The methods described herein may also provide treatments that are drug-free, very fast and leave no scar, and may be treated with only one or a few treatments. Alternatively, in some variations the methods of treatment using any of the resistively loaded dielectric biconical antenna apparatuses described herein may include the concurrent use of one or more drugs or other active agents, local and/or systemic.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the apparatus in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A resistively loaded antenna system, the system comprising:
    a proximal wave-launching section comprising a solid cone of dielectric material and one or more pairs of conducive plates extending over a portion of the cone of dielectric material;
    a waveguide extending distally from a base of the solid cone of dielectric material;
    a distal wave-emitting section coupled to the waveguide; and
    a resistor ring electrically connecting the one or more pairs of conductive plates and extending laterally at least partially around the distal wave-emitting section.

2. The system of claim 1, wherein the conductive plates comprise triangular conductive plates.

3. The system of claim 1, wherein the dielectric material is a low-epsilon material.

4. The system of claim 1, wherein the dielectric material is a high dielectric material.

5. The system of claim 1, wherein the dielectric material has a dielectric constant of between 3 and 20.

6. The system of claim 1, wherein the resistor ring is configured to reduce electrical reflection of nanosecond and sub-nanosecond pulses.

7. The system of claim 1, wherein the resistor ring is configured to provide impedance matching to absorb energy so that low frequency energy applied to the proximal end does not get reflected back from the distal wave-emitting section.

8. The system of claim 1, wherein the resistor ring comprises a mixture of a polymeric material and conductive carbon, or comprises a conductive polylactic acid (PLA) and conductive carbon black.

9. The system of claim 1, wherein the waveguide is cylindrical and has a width in a proximal-to-distal direction that is less than 10% of the length of the proximal wave-launching section in the proximal-to-distal direction.

10. The system of claim 1, further comprising an oil-filled cover enclosing at least the proximal wave-launching section and the waveguide.

11. The system of claim 1, further comprising a feed coupled to a proximal end of the proximal wave-launching section.

12. The system of claim 11, wherein the feed comprises two parallel plates with a dielectric liner.

13. The system of claim 11 further comprising a coaxial cable electrically coupled to the feed.

14. The system of claim 13, further comprising a high-voltage pulse generator configured to couple to the coaxial cable.

15. The system of claim 14, wherein the pulse generator is configured to generate a series of pulses having a pulse width of between about 1 picosecond (ps) and 10 nanoseconds (ns).

16. The system of claim 14, wherein the pulse generator is configured to generate a series of pulses having a magnitude of between about 1 kV and 1 MV.

17. The system of claim 1, wherein the dielectric material has a dielectric constant of greater than 20.

18. A method of treatment of biological tissue, the method comprising:
- placing a distal wave-emitting section of the resistively loaded antenna against a tissue;
- applying a plurality of sub-microsecond pulses from a pulse generator to one or more pairs of conducive plates extending over a proximal section of the resistively loaded antenna, wherein the one or more pairs of conductive plates are electrically connected through a resistor ring configured to prevent or limit reflection of electrical energy back towards the pulse generator; and
- delivering the sub-microsecond waves of electrical energy to the tissue in a region that is focused between 0.1 and 5 cm from a distal end of the resistively loaded antenna.

19. The method of claim 18, the method comprising coupling the resistively loaded antenna to the pulse generator.

20. The method of claim 18, wherein applying comprises passing the plurality of sub-microsecond pulses through a cylindrical waveguide extending distally from a base of the proximal section and into the distal wave-emitting section.

21. The method of claim 20, wherein the cylindrical waveguide has a width in a proximal-to-distal direction that is less than 10% of the length of the proximal wave-launching section in the proximal-to-distal direction.

22. The method of claim 18, wherein applying the plurality of sub-microsecond pulses comprises applying a train of sub-microsecond pulses having a magnitude of between about 1 kV and 1 MV.

23. The method of claim 18, wherein applying the plurality of sub-microsecond pulses comprises applying a train of sub-nanosecond pulses having a frequency of between 1 Hz and 1 GHz.

24. The method of claim 18, further comprising delivering microsecond or millisecond pulses through the resistor ring to the tissue.

* * * * *